(12) United States Patent
Watanabe et al.

(10) Patent No.: US 9,452,341 B2
(45) Date of Patent: Sep. 27, 2016

(54) RUNNING FORM DIAGNOSIS SYSTEM AND METHOD FOR SCORING RUNNING FORM

(71) Applicant: Mizuno Corporation, Osaka (JP)

(72) Inventors: Yoshinobu Watanabe, Osaka (JP); Yasuyuki Ohta, Osaka (JP); Daisuke Kogawa, Osaka (JP); Yohei Yoshida, Osaka (JP); Naoki Yoshikawa, Osaka (JP)

(73) Assignee: Mizuno Corporation, Osaka (JP)

( * ) Notice: Subject to any disclaimer, the term of this patent is extended or adjusted under 35 U.S.C. 154(b) by 196 days.

(21) Appl. No.: 14/116,971

(22) PCT Filed: Feb. 28, 2013

(86) PCT No.: PCT/JP2013/055517
§ 371 (c)(1),
(2) Date: Jan. 23, 2014

(87) PCT Pub. No.: WO2013/129606
PCT Pub. Date: Sep. 6, 2013

(65) Prior Publication Data
US 2014/0148931 A1 May 29, 2014

(30) Foreign Application Priority Data

Feb. 29, 2012 (JP) .................... 2012-044622

(51) Int. Cl.
*A63B 71/06* (2006.01)
*A61B 5/11* (2006.01)
(Continued)

(52) U.S. Cl.
CPC ............ *A63B 71/06* (2013.01); *A61B 5/1121* (2013.01); *A61B 5/1124* (2013.01); *A61B 5/1127* (2013.01);
(Continued)

(58) Field of Classification Search
CPC ........................... A63B 2230/00; A61B 5/04
See application file for complete search history.

(56) References Cited

U.S. PATENT DOCUMENTS 6,056,671 A * 5/2000 Marmer ............... A61B 5/1124
482/10
2006/0166737 A1 7/2006 Bentley
(Continued)

FOREIGN PATENT DOCUMENTS

CA 2819067 A1 6/2012
CN 2726530 Y 9/2005
(Continued)

OTHER PUBLICATIONS

Chinese Office Action dated Dec. 29, 2014 for Chinese Patent Application No. 201380001601.8.
(Continued)

*Primary Examiner* — James S McClellan
*Assistant Examiner* — Syvila Weatherford
(74) *Attorney, Agent, or Firm* — Troutman Sanders LLP; James Schutz; Daniel Sharpe

(57) ABSTRACT

A running form diagnosis system capable of automatically scoring a running form of a runner is provided. The running form diagnosis system obtains body motion information as to a test subject running on a treadmill, and calculate a running form score of the test subject by applying obtained characteristics to a given operation expression. The operation expression is generated based on correlation between characteristics of a plurality of test runners and comprehensive evaluation given by an expert with respect to the plurality of test runners.

11 Claims, 28 Drawing Sheets

(51) Int. Cl.
*A63B 5/04* (2006.01)
*A61B 5/00* (2006.01)

(52) U.S. Cl.
CPC ............... *A61B 5/742* (2013.01); *A61B 5/744* (2013.01); *A61B 2503/10* (2013.01); *A63B 5/04* (2013.01); *A63B 2230/00* (2013.01)

(56) References Cited

U.S. PATENT DOCUMENTS

| | | | |
|---|---|---|---|
| 2009/0170663 | A1 | 7/2009 | Cox et al. |
| 2009/0220124 | A1* | 9/2009 | Siegel ............... G06K 9/00342 382/103 |
| 2012/0172682 | A1* | 7/2012 | Linderman .......... A61B 5/0476 600/301 |
| 2012/0231840 | A1* | 9/2012 | Calman .............. G06K 9/00342 455/556.1 |

FOREIGN PATENT DOCUMENTS

| | | |
|---|---|---|
| CN | 201928342 U | 8/2011 |
| JP | 2002-233517 | 8/2002 |
| JP | 2002253718 A | 9/2002 |
| JP | 2009297295 A | 12/2009 |
| JP | 2010-17447 | 1/2010 |
| JP | 2011041752 A | 3/2011 |
| JP | 201224275 A | 2/2012 |
| WO | 2006081395 A2 | 8/2006 |
| WO | 2011163367 A1 | 12/2011 |

OTHER PUBLICATIONS

International Search Report mailed Apr. 9, 2013 for related International Application No. PCT/JP2013/055517.
European Search Report completed Dec. 4, 2014 for related European Application No. EP13755578.
Lilley, Kim Louise: "A Biomechanical Assessment of Gait Patterns and Risk of Associated Overuse Conditions among Mature Female Runners", PhD thesis, Feb. 3, 2012, pp. 1-412, XP055155593, Retrieved from the Internet: URL: https://ore.exeter.ac.uk/repository/bitstream/handle/10036/3492/LilleyK.pdf?sequence=2 [retrieved on Nov. 27, 2014].
Lilley, Kim Louise: "Proof date: A Biomechanical Assessment of Gait Patterns and Risk of Associated Overuse Conditions among Mature Female Runners", Feb. 3, 2012, XP055155681, Retrieved from the Internet: URL: https://ore.exeter.ac.uk/repository/handle/10036/3492 [retrieved on Nov. 27, 2014].
Fleming, Paul et al.: "Athlete and coach perceptions of technology needs for evaluating running performance", Sports Engineering, vol. 13, No. 1, Aug. 14, 2010, pp. 1-18, XP055155601, ISSN: 1369-7072, DOI: 10.1007/s12283-010-0049-9.
International Search Report dated Apr. 9, 2013 for co-pending International Application No. PCT/JP2013/055517.
Office Action in related Canadian Patent Application No. CA2834833, mailed Apr. 13, 2015.
Examination Report in related European Patent Application No. EP13755578.5, mailed Oct. 15, 2015.

* cited by examiner

UPPER ARM ANGLE (SIDE) Max

LOWER LEG ANGULAR DIFFERENCE − THIGH ANGULAR DIFFERENCE

Score 1 = N1 + N2 × BMI ...(1)
Score 2 = I1 + I2 × THIGH ANGLE (REAR) MaxMin ...(2)
Score 3 = J1 + J2 × FOREARM ANGLE (SIDE) MaxMin ...(3)
Score 4 = K1 + K2 × UPPER ARM ANGLE (SIDE) Max ...(4)
Score 5 = L1 + L2 × (LOWER LEG ANGULAR DIFFERENCE
        − THIGH ANGULAR DIFFERENCE) ...(5)
Score 6 = M1 + M2 × THIGH ANGULAR VELOCITY (SIDE) Min ...(6)

USER CHARACTERISTICS $X_n$
HIGHLY CORRELATED WITH SKILL
ELEMENT $F_n$ CONSTITUTING
COMPREHENSIVE SCORE

COMPREHENSIVE
EVALUATION SCORE

FIG.23

| PERSON MAKING ENTRY／ | | | | | | | | |
|---|---|---|---|---|---|---|---|---|
| SUB1 | | | | | | | | |
| SENSE OF SPEED | PRESENT ← | | | | | | → ABSENT | |
| | 7 | 6 | 5 | 4 | 3 | 2 | 1 | |
| BEAUTY | PRESENT ← | | | | | | → ABSENT | |
| | 7 | 6 | 5 | 4 | 3 | 2 | 1 | |
| SAFENESS | PRESENT ← | | | | | | → ABSENT | |
| | 7 | 6 | 5 | 4 | 3 | 2 | 1 | |
| SENSE OF RHYTHM | PRESENT ← | | | | | | → ABSENT | |
| | 7 | 6 | 5 | 4 | 3 | 2 | 1 | |
| RELAX | PRESENT ← | | | | | | → ABSENT | |
| | 7 | 6 | 5 | 4 | 3 | 2 | 1 | |
| DYNAMISM | PRESENT ← | | | | | | → ABSENT | |
| | 7 | 6 | 5 | 4 | 3 | 2 | 1 | |
| SMOOTH | PRESENT ← | | | | | | → ABSENT | |
| | 7 | 6 | 5 | 4 | 3 | 2 | 1 | |
| BALANCE | PRESENT ← | | | | | | → ABSENT | |
| | 7 | 6 | 5 | 4 | 3 | 2 | 1 | |
| COMPREHENSIVE EVALUATION | GOOD ← | | | | | | → BAD | |
| | 100 | | | 50 | | | 0 | |
| | | | | | | SCORE | | |

FIG.26

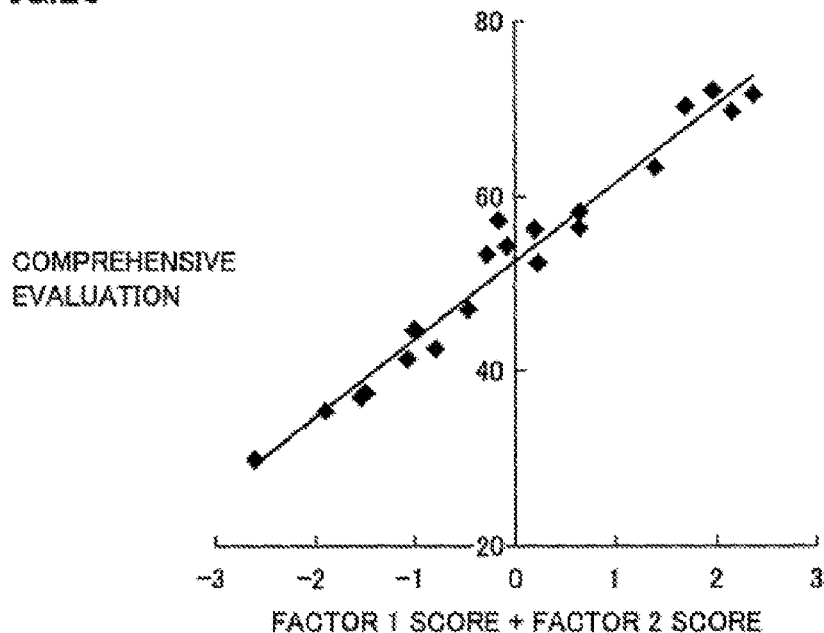

FIG.27

Safety = A1 + A2 × BMI + THIGH ANGLE (REAR) MaxMin ...(7)
Relax = B1 + B2 × FOREARM ANGLE (SIDE) MaxMin ...(8)
"SAFENESS SCORE" = F1 + F2 × Safety + F3 × Relax ...(9)

Positioning = C1 + C2 × UPPER ARM ANGLE (SIDE) Max ...(10)
Ride = D1 + D2 × (LOWER LEG ANGULAR DIFFERENCE − THIGH ANGULAR
DIFFERENCE) + D3 × THIGH ANGULAR VELOCITY SIDE Min ...(11)
Swing = E1 + E2 × LOWER LEG ANGULAR VELOCITY_GROUND + E3 ×
LOWER LEG ANGLE (SIDE) Min ...(12)
"DYNAMISM SCORE" = G1 + G2 × Positioning + G3 × Ride + G4 × Swing ...(13)

COMPREHENSIVE SCORE =
H1 + H2 × "SAFENESS SCORE" + H3 × "DYNAMISM SCORE" ...(14)

RUNNING FORM DIAGNOSIS SYSTEM AND METHOD FOR SCORING RUNNING FORM

CROSS-REFERENCE TO RELATED APPLICATIONS

This application is a US National Stage of International Application No. PCT/JP2013/055517, filed Feb. 28, 2013, which claims the benefit of JP2012-044622, filed Feb. 29, 2012, both of which are herein fully incorporated by reference as if set forth below.

TECHNICAL FIELD

The present disclosure relates to a technology for automatically diagnosing a running form of a runner.

BACKGROUND ART

Conventionally, a diagnosis for a form of running, walking, golf, or the like is generally conducted based on individual determination with visual observation performed by an expert trainer or a coach. On the other hand, in recent years, there has been proposed various kinds of diagnosis systems for automatically conducting such a form diagnosis.

For example, Japanese Patent Laying-Open No. 2002-233517 (PTD 1) discloses an apparatus for evaluating the beauty of walking. The apparatus uses a pressure sensor to measure a foot pressure distribution of a walking test subject, and finds a track of foot pressure center of the test subject based on the measurement result. Then, the apparatus compares the track of foot pressure center of the test subject found in such a manner with a parameter of a model track of foot pressure center set in advance to grade the test subject's beauty of walking.

Japanese Patent Laying-Open No. 2010-017447 (PTD 2) discloses an apparatus for analyzing a walking state of a walker. The apparatus constructs a 3D human model based on a plurality of captured images to create data of a walking motion of the walker. Then, the data of the walking motion of the walker is compared with a walking motion of a normal person registered in dictionary data to analyze a walking state of the walker.

CITATION LIST

Patent Document

PTD 1: Japanese Patent Laying-Open No. 2002-233517
PTD 2: Japanese Patent Laying-Open No. 2010-017447

SUMMARY OF INVENTION

Technical Problem

However, all the conventional apparatuses described above compare measurement data of a test subject with specific data to conduct evaluation as to a motion of the test subject based on the result of comparison. Such apparatuses have a problem that evaluation results differ significantly depending on how data for use in comparison is selected. Therefore, a technology for suppressing variation in the evaluation results is demanded.

Further, there is a case where the data for use in comparison according to the conventional apparatuses does not strictly reflect an evaluation standard of an expert. In such a case, there is also a problem that a result of evaluation obtained with use of the data is less accurate as compared to a diagnosis result actually evaluated by an expert. Therefore, a technology of maintaining accuracy in a diagnosis result is required.

The present disclosure was achieved to solve the conventional problems described above, and its object is to provide a running form diagnosis system capable of automatically scoring a running form of a runner based on a standard equivalent to a determination given by an expert.

Solution to Problem

According to one aspect, a running form diagnosis system for scoring a running form of a test object is provided. The running form diagnosis system includes a storage device configured to store an operation expression representing a correlation between body motion information extracted from information related to running of a plurality of test runners and evaluation given by an expert with respect to respective running of the plurality of test runners, an interface for receiving an input of information related to running of the test subject, and a processor configured to output a score as to a running form of the test subject based on information inputted to the interface. The processor is configured to extract body motion information of the test subject from the information related to running of the test subject and inputted to the interface, and calculate the score as to the running form of the test subject by applying the extracted body motion information to the operation expression.

Preferably, the operation expression includes a first regression expression obtained by performing a regression analysis, with evaluation for two or more items given by the expert with respect to running of the test runners as an explanatory variable and with comprehensive evaluation given by the expert with respect to running of the test runners as an objective variable, and a second regression expression obtained by performing a regression analysis, with body motion information of the test runners as an explanatory variable and with respective evaluation for two or more items given by the expert with respect to the test runners as an objective variable.

Preferably, the two or more items used in the first regression expression are specified from a predetermined number of items by statistically processing evaluation for the predetermined number of items given by the expert with respect to running of the test runners and comprehensive evaluation given by the expert with respect to running of the test runners.

More preferably, the body motion information of the test runners used in the second regression expression is specified from characteristics of a specified number of items by statistically processing a specified number of body motion information and evaluation for the two or more items.

Preferably, the operation expression includes a multiple regression expression obtained by performing a multiple regression analysis, with a plurality of body motion information of the test runners as an explanatory variable and with comprehensive evaluation given by the expert with respect to the test runners as an objective variable.

Preferably, the operation expression includes a plurality of regression expressions obtained by performing a regression analysis, with a plurality of body motion information of the test runners as an explanatory variable and with comprehensive evaluation given by the expert with respect to the test runners as an objective variable. The processor calculates a score of the running form of the test subject based on a plurality of comprehensive evaluations obtained by the plurality of regression expressions. Preferably, the body motion information of the test subject includes at least any of an elbow joint angle obtained by calculating an angle of a forearm with respect to an upper arm of the test subject, respective segment angles of the forearm and the upper arm of the test subject, a knee joint angle obtained by calculating an angle of a lower leg with respect to an upper leg of the test subject, or respective segment angles of the lower leg and the upper leg of the test subject.

Preferably, the running form diagnosis system further includes an image-capturing device coupled to the interface to capture a picture of the test subject. The interface is configured to receive an input of the picture of the test subject. The processor is configured so that when extracting at least any of the elbow joint angle of the test subject or the respective segment angles of the forearm and the upper arm of the test subject, the processor extracts these angles based on positions of images of markers attached to a shoulder joint, an elbow joint, and a wrist joint of the test subject in the picture, and when extracting at least any of the knee joint angle of the test subject or the respective segment angles of the lower leg and the upper leg of the test subject, the processor extracts these angles based on positions of images of markers attached to a hip joint, a knee joint, and an ankle joint of the test subject in the picture.

Preferably, the running form diagnosis system further includes an inertial sensor attached to the test subject. The interface is configured to receive an input of a detection result of the inertial sensor. The processor is configured to extract body motion information of the test subject based on the detection result of the inertial sensor.

Preferably, the storage device is configured to store advice information as to running in association with scores grouped in advance. The processor is configured to output the advice information associated with the scores calculated for the test subject.

Preferably, the operation expression further represents a correlation between body motion information extracted from information related to running of the plurality of test runners as well as body characteristics of the plurality of test runners and comprehensive evaluation given by the expert with respect to respective running of the plurality of test runners. The interface is further configured to receive an input of the body characteristics of the test subject. The processor is configured to calculate a score as to the running form of the test subject by applying the body motion information and body characteristics of the test subject to the operation expression.

According to another aspect, a method for scoring a running form of a test subject is provided which is executed by a computer. The computer includes a storage device configured to store an operation expression representing a correlation between body motion information extracted from information related to running of a plurality of test runners and comprehensive evaluation given by an expert with respect to respective running of the plurality of test runners, and an interface for receiving an input of information related to running of the test subject. The method includes allowing the computer to extract body motion information of the test subject from information related to running of the test subject and inputted to the interface, and allowing the computer to calculate a score as to the running form of the test subject by applying the extracted body motion information to the operation expression.

Preferably, the operation expression includes a first regression expression obtained by performing a regression analysis, with evaluation for two or more items given by the expert with respect to running of the test runners as an explanatory variable and with a score given by the expert with respect to running of the test runners as an objective variable, and a second regression expression obtained by performing a regression analysis, with body motion information of the test runners as an explanatory variable and with respective evaluation for two or more items given by the expert with respect to the test runners as an objective variable.

Preferably, the operation expression includes a multiple regression expression obtained by performing a multiple regression analysis, with a plurality of body motion information of the test runners as an explanatory variable and with comprehensive evaluation given by the expert with respect to the test runners as an objective variable.

Preferably, the operation expression includes a plurality of regression expressions obtained by performing a regression analysis, with a plurality of respective body motion information of the test runners as an explanatory variable and with comprehensive evaluation given by the expert with respect to the test runners as an objective variable. Allowing the computer to calculate a score as to the running form of the test subject includes calculating a score as to the running form of the test subject based on a plurality of comprehensive evaluation obtained from the plurality of regression expressions.

The above-described and other object, feature, aspect, and advantage of the present invention will be apparent from the following detailed description of the invention to be understood with reference to the attached drawings.

BRIEF DESCRIPTION OF DRAWINGS

FIG. 23 represents a specific example of the questionnaire distributed to the expert.

FIG. 26 represents correlation between factor scores of the extracted factors and "comprehensive evaluation."

FIG. 27 represents an example of a set of expressions used for calculating the running form score.

FIG. 32 represents a specific example of an output sheet.

FIG. 33 represents a specific example of an output sheet.

DESCRIPTION OF EMBODIMENTS

Hereinafter, an embodiment of a running form diagnosis system will be described with reference to the drawings. In the following description, the same parts have the same reference signs allotted. Names and functions of these are the same. Therefore, detailed description about these parts are not repeated.

[Configuration of Running Form Diagnosis System]

Figure 1:
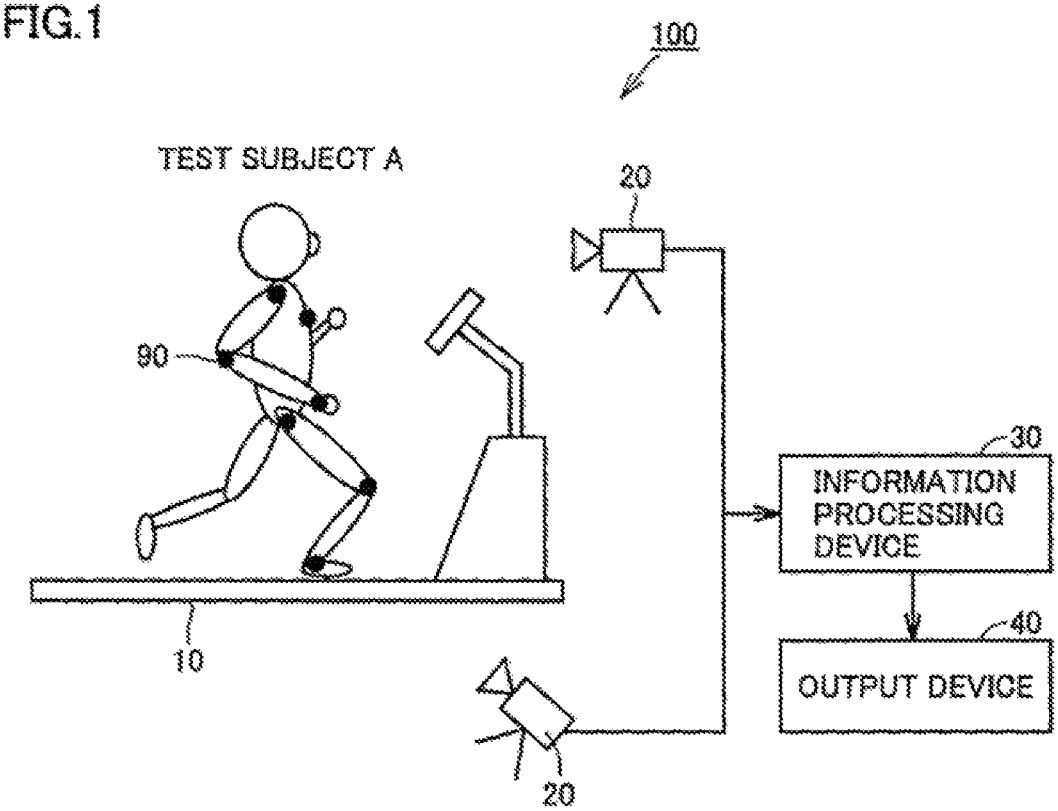
FIG. 1 represents a configuration of a running form diagnosis system.

An example of a configuration of a system including one embodiment of the running form diagnosis system will be described. FIG. 1 represents a configuration of a running form diagnosis system 100.

As shown in FIG. 1, running form diagnosis system 100 includes a treadmill 10, an image-capturing system 20 for capturing an image of a test subject A wearing markers 90, an information processing device 30 for scoring a running form of test subject A based on a picture of running test subject A, and an output device 40 for outputting a diagnosis result of a running form of test subject A. Test subject A wears markers 90, for example, at six locations on the right side (shoulder, elbow, wrist, thigh base, knee, and ankle) respectively. Information processing device 30 obtains body characteristics of test subject A and also extracts body motion information of test subject A from picture data of running test subject A. Then, information processing device 30 calculates a running form score of the test subject based on the body characteristics and/or the body motion information. The running form diagnosis system includes at least information processing device 30.

As shown in FIG. 1, image-capturing system 20 may be configured by a system including, for example, two high-speed cameras as shown in FIG. 1 and capable of using a motion-capture technology. Information processing device 30 includes a CPU (Central Processing Unit), a storage device, software, and the like, and is configured by, for example, a PC (personal computer). A detailed configuration of information processing device 30 will be described later. Output device 40 is configured by a monitor and/or a printer visually outputting information. Output device 40 may output a diagnosis result in a form of sound or the like other than image, or in combination of two or more output forms such as audiovisual information.

[Hardware Configuration of Information Processing Device 30]

Figure 2:
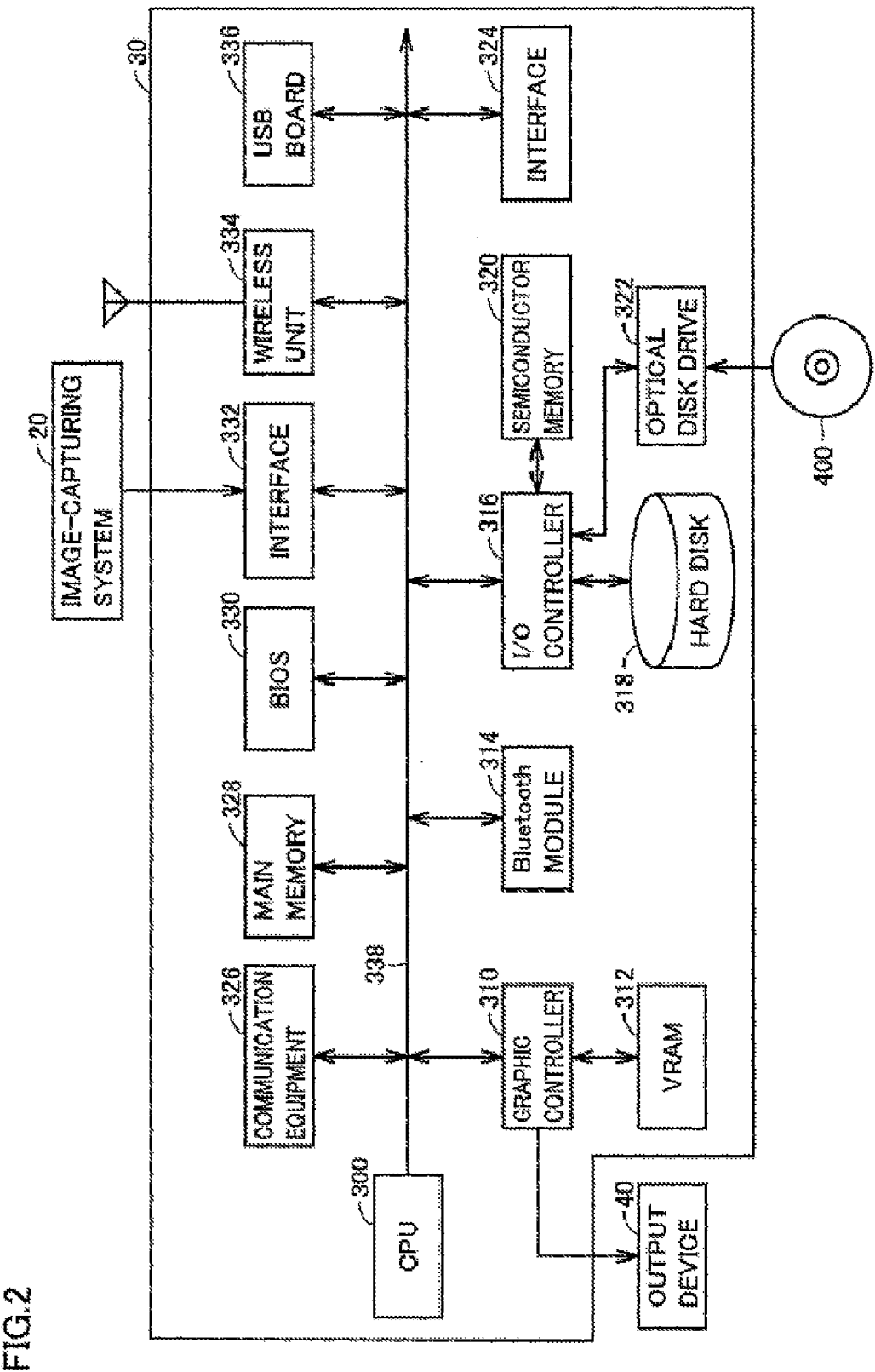
FIG. 2 represents an example of a hardware configuration of an information processing device.

With reference to FIG. 2, an example of a hardware configuration of information processing device 30 will be described. FIG. 2 represents an example of a hardware configuration of information processing device 30.

Information processing device 30 includes a CPU 300, a graphic controller 310, a VRAM (Video RAM (Random Access Memory)) 312, an I/O (input/output) controller 316, interfaces 324, 332, communication equipment (interface) 326, a main memory 328, a BIOS (Basic Input Output System) 330, a USB (Universal Serial Bus) board 336, and a bus line 338.

BIOS 330 stores a boot program executed by CPU 300 at the time of booting information processing device 30, programs dependent on hardware of information processing device 30, and the like. Storage devices such as a hard disk 318, an optical disk drive 322, a semiconductor memory 320, and the like are connected to I/O controller 316. Interface 324 is a device such as a touch panel, a keyboard, and the like for inputting information to information processing device 30.

Interface 332 is an example of an interface for inputting picture data from image-capturing system 20 to information processing device 30. Graphic controller 310 is an example of an interface for outputting information from information processing device 30 to output device 40, and uses VRAM 312.

Information processing device 30 further includes a wireless unit 334 and a Bluetooth (Registered Trademark) module 314. Information processing device 30 can communicate wirelessly with external equipment via wireless unit 334. Further, information processing device 30 can communicate with external equipment in the Bluetooth method (an example of a near field communication method) with use of Bluetooth module 314.

As optical disk drive 322, for example, a CD-ROM (Compact Disc-ROM (Read Only Memory)) drive, a DVD (Digital Versatile Disc)-ROM drive, a DVD-RAM drive, and/or a BD (Blu-ray Disk)-ROM drive may be employed. Optical disk 400 is a recording medium in a format compatible with optical disk drive 322. CPU 300 reads a program or data from optical disk 400 using optical disk drive 322. CPU 300 allows the read program or data to be loaded to main memory 328 or installed into hard disk 318 via I/O controller 316. Communication equipment 326 is equipment mounted to information processing device 30 for communication with other equipment such as a LAN (Local Area Network) card and the like.

CPU 300 can execute a program which may be stored in optical disk 400 or a recording medium (memory card and the like) and provided to a user. CPU 300 may execute a program stored in a recording medium other than optical disk 400 or may execute a program downloaded via communication equipment 326.

[Overall Operation of Running Form Diagnosis System]

Figure 3:
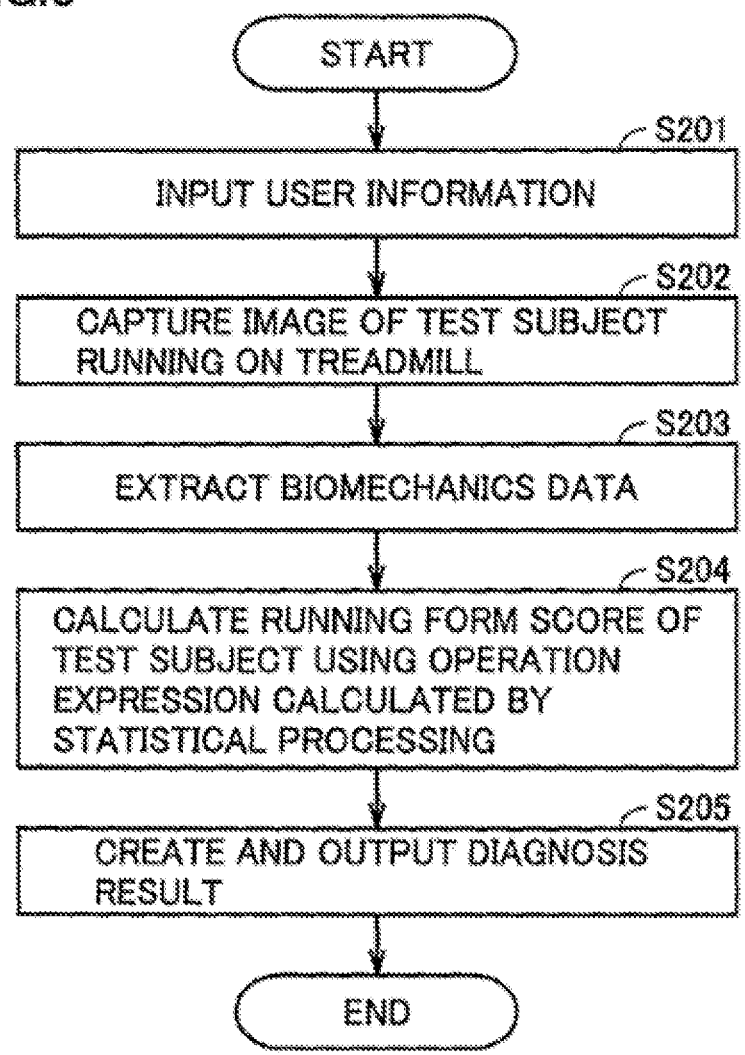
FIG. 3 is a flowchart representing operation of the running form diagnosis system.

Hereinafter, operation of running form diagnosis system 100 will be described with reference to FIGS. 1-3. FIG. 3 is a flowchart representing operation of running form diagnosis system 100.

First, in Step S201, user information such as height, weight, gender, or amount of practice per month of test subject A is inputted to information processing device 30. CPU 300 receives input of the user information.

Next, image-capturing system 20 captures an image of test subject A wearing markers 90 and running on treadmill 10 for a certain period of time (Step S202). Moving picture data generated by capturing image is outputted to information processing device 30.

Next, information processing device 30 extracts biomechanics data (body motion information) such as a joint angle, an angular velocity, and the like from picture data transmitted from image-capturing system 20 (Step S203). CPU 300 handles picture data between grounding of the right foot of test subject A and next grounding of the right foot as one cycle of data. In Step S203, CPU 300, for example, extracts respective biomechanics data from a plurality of cycles and calculates an average value of these. Kinds of biomechanics data will be described later.

Next, information processing device 30 calculates a running form score of the test subject (Step S204) by applying characteristics of the user (the biomechanics data of the test subject extracted in Step S203 and/or body characteristics of the test subject) to a given operation expression. The given operation expression is derived, for example, by statistically processing evaluation points given by a plurality of experts (evaluators) to running forms of a plurality of runners in the past and biomechanics data of the plurality of runners.

Then, information processing device 30 creates an output sheet presenting a running form score together with advice information as to a running form, and displays it on output device 40 (Step S205). The display terminates a series of operation of running form diagnosis system 100.

[Function of Information Processing Device]

Figure 4:
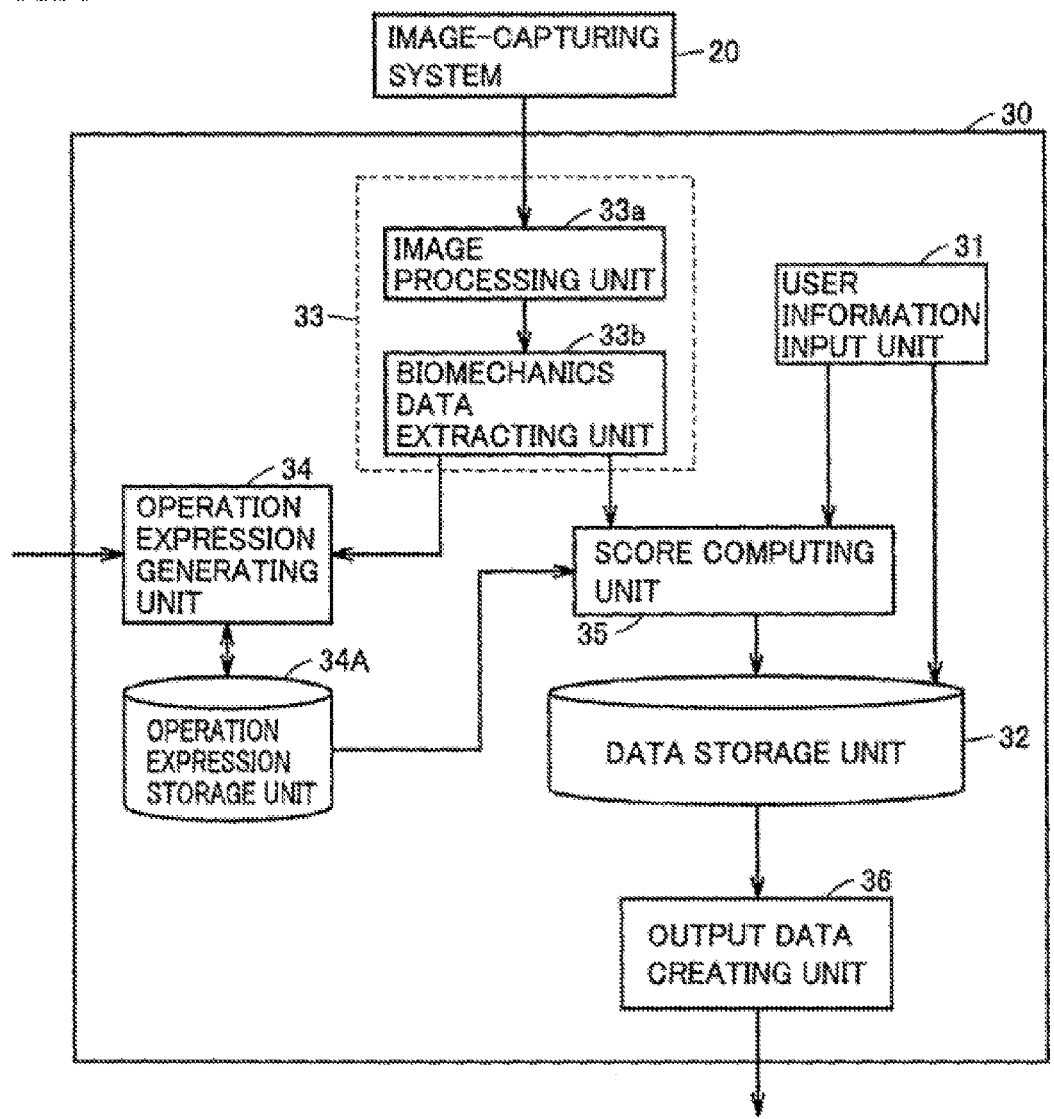
FIG. 4 is a block diagram representing a functional configuration of the information processing device.

With reference to FIG. 4, a functional configuration of information processing device 30 will be described. FIG. 4 is a block diagram representing a functional configuration of information processing device 30. As shown in FIG. 4, information processing device 30 includes a user information input unit 31, a data storage unit 32, a body information extracting unit 33, an operation expression generating unit 34, an operation expression storage unit 34A, a score computing unit 35, and an output data creating unit 36.

User information input unit 31 is an interface for receiving an input of user information such as height, weight, treadmill speed, amount of practice per month, and the like of the test subject and is constituted by a keyboard, a touch panel, and the like. Inputted various kinds of information is stored in data storage unit 32. In addition to storing various kinds of computing data, data storage unit 32 stores output data creating data such as an evaluation comment as to a running form, advice information as to improvement of a running form, and the like given by an expert. Score computing unit 35 and output data creating unit 36 suitably use information stored in data storage unit 32.

Body information extracting unit 33 extracts biomechanics data such as a joint angle, a joint angular velocity, and the like from a running picture of test subject A transmitted from image-capturing system 20 via an interface (interface 332 of FIG. 2). As shown in FIG. 4, body information extracting unit 33 includes an image processing unit 33a and a biomechanics data extracting unit 33b.

Image processing unit 33a measures positions of the markers in the running picture of test subject A transmitted from image-capturing system 20 to derive 3D coordinate values related to the motion of test subject A. Image processing unit 33a is implemented, for example, by CPU 300 executing software for performing motion-capture processing. The 3D coordinate value information extracted in image processing unit 33a is transmitted to biomechanics data extracting unit 33b.

Biomechanics data extracting unit 33b extracts biomechanics data of test subject A from the 3D coordinate value information outputted from image processing unit 33a. More specifically, biomechanics data extracting unit 33b calculates a joint angle and a joint angular velocity of test subject A based on the 3D coordinate value information outputted from image processing unit 33a. Further, biomechanics data extracting unit 33b calculates a segment angle (segment angular velocity) projected to each plane of an absolute coordinate system by applying each joint angle (joint angular velocity) to a given conversion expression.

Biomechanics data extracting unit 33b further calculates respective processed data for the joint angle, joint angular velocity, segment angle, and segment angular velocity. The processed data includes a maximum value, a minimum value, and/or a difference between the maximum value and the minimum value (hereinafter, also referred to as "maximum value—minimum value"). The processed data may include in some cases a joint angle and an angular velocity at a given time when the time taken by one foot of the test subject for ground contact and getting off the ground is standardized.

Biomechanics data extracting unit 33b is implemented for example by CPU 300 executing a given program. In the present embodiment, biomechanics data may include the joint angle, joint angular velocity, segment angle, and segment angular velocity as mentioned above, and processed data of these. The extracted biomechanics data is outputted from biomechanics data extracting unit 33b to score computing unit 35.

Operation expression generating unit 34 generates the operation expression described above. Information specifying the generated operation expression is stored in operation expression storage unit 34A. Operation expression generating unit 34 is implemented, for example, by CPU 300 executing a given program. Generation of the operation expression by operation expression generating unit 34 will be described later with reference to FIG. 5.

Score computing unit 35 reads out from operation expression storage unit 34A the operation expression generated by operation expression generating unit 34. Then, score computing unit 35 calculates a running form score of the test subject by applying the biomechanics data outputted from biomechanics data extracting unit 33b to the operation expression. Calculation of the running form score by score computing unit 35 corresponds to Step S204 in FIG. 3. Score computing unit 35 is achieved, for example, by CPU 300 executing a given program.

Score computing unit 35 outputs the calculated running form score to output data creating unit 36. Output data creating unit 36 generates a diagnosis result by combining the calculated running form score with a running picture of test subject A cut out in image processing unit 33a, running advice data stored in data storage unit 32, and/or the like. The diagnosis result is displayed as an output sheet on output device 40. The diagnosis result may be printed out as needed in some cases. Output data creating unit 36 is implemented, for example, by CPU 300 executing a given program. The processing in which output data creating unit 36 allows output device 40 and the like to output the diagnosis result corresponds to the processing of Step S205 in FIG. 3.

The diagnosis result may include in some cases, in addition to advice information, information related to running shoes and wears suitable for the running form of the test subject. In other words, data storage unit 32 may store characteristics information of optimum running shoes and/or specific product information corresponding to the running form score and the body motion information of the test subject in advance as a data table. Then, based on user information inputted to user information input unit 31, a finally obtained running form score of the test subject, and/or body information of the test subject, output data creating unit 36 reads the data table described above, selects optimum running shoes information, and adds the same to a diagnosis result. Further, information specifying a running wear corresponding to the running form score and/or the body motion information of the test subject may be included in the data table in some cases. In this case, the running form diagnosis system may present information of the optimum running wear to the test subject as a diagnosis result.

As described above, according to the running form diagnosis system in accordance with the present embodiment, the operation expression is prepared based on a correlation between biomechanics data obtained from pictures of running test runners and the running form scores given to running of the test runners by a plurality of experts. Then, a running form score of the test subject is calculated by applying the biomechanics data of the test subject extracted from a running picture of the test subject to the operation expression. The operation expression described above is generated based on a determination standard common to the plurality of experts. Therefore, in the present embodiment, a running form score calculated based on the determination standard of the plurality of experts is given with respect to running of the test subject. Therefore, the accuracy of the given running form score can be improved.

In the present embodiment, the test runner means a data-collection runner for use in calculating a running form score of a test subject. In other words, in the present embodiment, the operation expression is generated based on running of the test runners, and the operation expression is used, so that the running form score of the test subject is calculated.

[Generation of Operation Expression]

Figure 5:
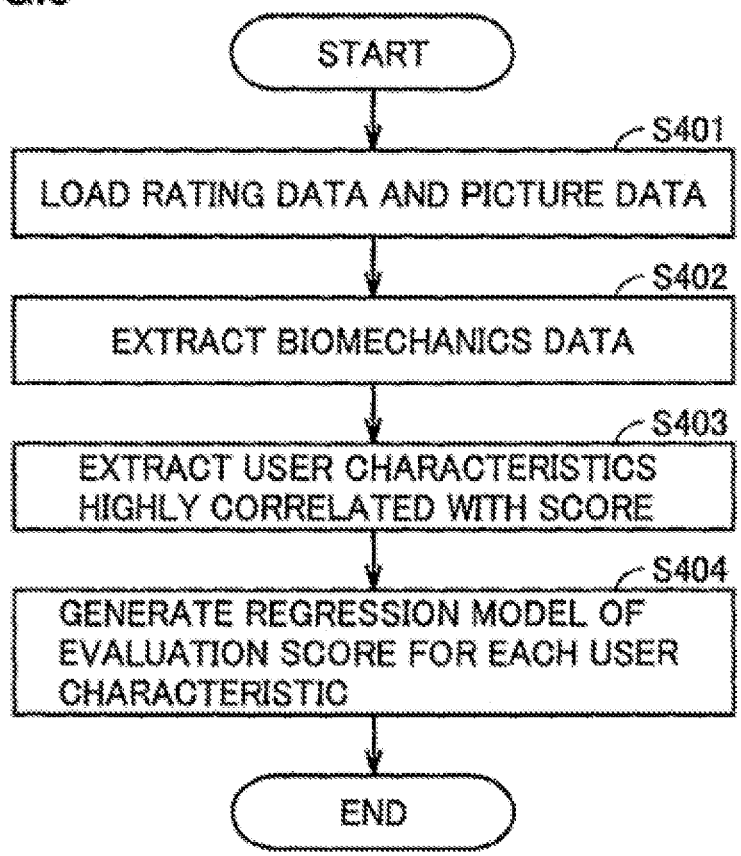
FIG. 5 is a flowchart representing generation of an operation expression.

The operation expression used by score computing unit 35 to calculate a running form score of the test subject is generated by operation expression generating unit 34. Herein, generation of the operation expression will be described with reference to FIG. 5. Hereinafter, generation of the operation expression will be described with reference to FIG. 5. FIG. 5 is a flowchart representing generation of the operation expression.

Referring to FIG. 5, when generating the operation expression, operation expression generating unit 34 loads, in Step S401, picture data of a plurality of running test runners and data of rating given by the expert to running forms of the plurality of test runners.

The picture data loaded in Step S401 will be described. As a preparation in advance for Step S401, a picture of a data-collection test runner running on a treadmill is prepared. Herein, pictures of a plurality of test runners are prepared. The pictures are captured, for example, by image-capturing system 20. For convenience in description, the number of test runners is denoted by "M." Preferably, the M number of test runners are selected so that characteristics such as a skill, gender, and age of the M number of runners are distributed as wide as possible. Further, preferably, all of the pictures of the test runners are captured under the same condition. For example, the picture of each test runner may include the one captured from at least the right side and rear side of the test subject. In Step S401, the picture data for the M number of test runners is loaded.

The rating data loaded in Step S401 will be described. Each of the plurality of experts gives a running form score for each test runner while watching running pictures of the M number of test runners. The rating data includes information specifying the running form scores given in this stage. For convenience in description, the number of experts is denoted by "N." As a preparation in advance for Step S401, rating data of the N number of experts for each of the M number of test runners is prepared. In Step S401, the prepared rating data of the N number of experts for the M number of test runners is loaded. As experts who give scores, a plurality of researchers and coaches specialized in running and sports biomechanics can be envisioned.

Figure 6:
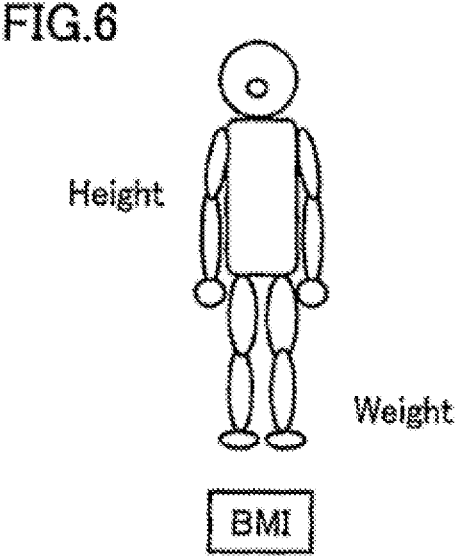
FIG. 6 is a drawing for describing a method for calculating a BMI (Body Math Index).

In Step S401, operation expression generating unit 34 may further load user information of each test runner to extract body characteristics of each test runner from the user information. The body characteristics include, in addition to user information inputted to user information input unit 31, information generated by processing the user information (for example, a BMI). FIG. 6 is a drawing for describing a method for calculating a BMI. As shown in FIG. 6, a BMI is calculated based on height and weight of a runner.

In Step S402, operation expression generating unit 34 extracts biomechanics data of each test runner from the picture data loaded in Step S401. Operation expression generating unit 34 can use functions of image processing unit 33a and biomechanics data extracting unit 33b to extract the biomechanics data.

Figure 7:
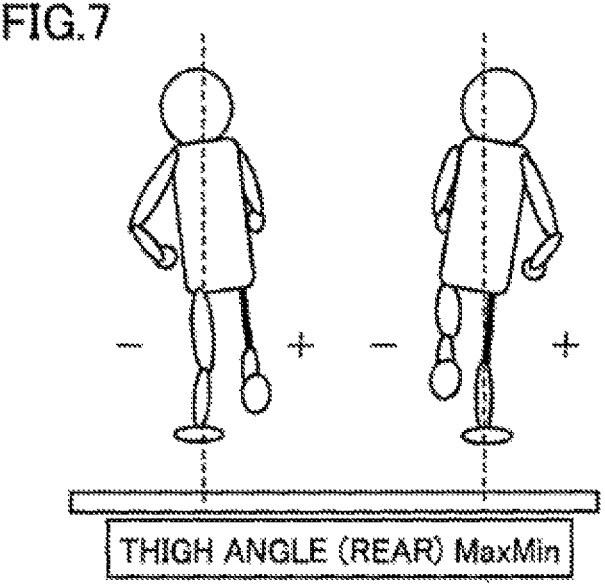
FIG. 7 is a drawing for describing "thigh angle (rear) MaxMin" as an example of biomechanics data.

Referring to FIGS. 7-13, a specific example of the biomechanism data will be described. FIGS. 7-13 are drawings for describing examples of the biomechanics data. Each of FIGS. 7-13 schematically represents a figure of a runner included in picture data. FIG. 7 represents figures of the runner at two different timings. In each of FIGS. 7-13, a reference line for obtaining biomechanics data is indicated by a broken line. Operation expression generating unit 34 specifies positions of limbs of the runner based on, for example, the positions of markers 90 (refer to FIG. 1) in the picture and defines each reference line. Each runner wears markers 90, for example, at six locations on the right side (shoulder, elbow, wrist, thigh base, knee, and ankle).

FIG. 7 represents an example of a picture of the runner captured from the rear side. FIGS. 8-13 represent examples of images of the runner captured from the right side. In FIGS. 7-13, a positive sign (+) is presented on one side with respect to the reference line and a negative sign (+) is presented on the other side. These signs indicate a relationship between a position of a subject part among four limbs of a runner in each drawing and a sign (positive or negative) of a value of biomechanics data extracted based on each drawing. In the following description as to the biomechanics data, "Max" represents a maximum value of an angle on the "+" side with respect to the reference line. "Min" represents a minimum value of an angle on the "−" side with respect to the reference line (a maximum value of an absolute value on the "−" side). "MaxMin" represents an angular difference between "Max" and "Min."

FIG. 7 is a drawing for describing "thigh angle (rear) MaxMin" as an example of biomechanics data. The "thigh angle (rear) MaxMin" is extracted based on an angle of a thigh with respect to the reference line. More specifically, operation expression generating unit 34 extracts from picture data a maximum value and a minimum value of an angle of the thigh with respect to the reference line in each cycle within a certain period of time, calculates respective average values of extracted maximum values and minimum values for a plurality of cycles, and calculates a difference between the average value of the maximum values and the average value of the minimum values to obtain "thigh angle (rear) MaxMin."

Figure 8:
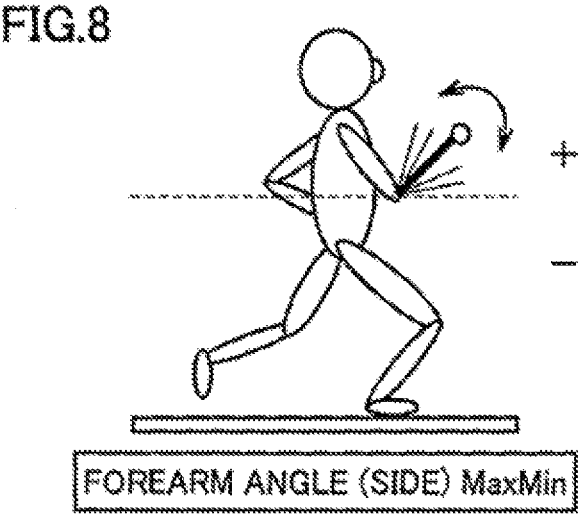
FIG. 8 is a drawing for describing "forearm angle (side) MaxMin" as an example of biomechanics data.

FIG. 8 is a drawing for describing "forearm angle (side) MaxMin" as an example of biomechanics data. The "forearm angle (side) MaxMin" is extracted based on an angle of the forearm with respect to the reference line. More specifically, operation expression generating unit 34 extracts from the picture data a maximum value and a minimum value of an angle of the forearm with respect to the reference line in each cycle within a certain period of time, calculates respective average values of extracted maximum values and minimum values for a plurality of cycles, and calculates a difference between the average value of the maximum values and the average value of the minimum values to obtain "forearm angle (side) MaxMin."

Figure 9:
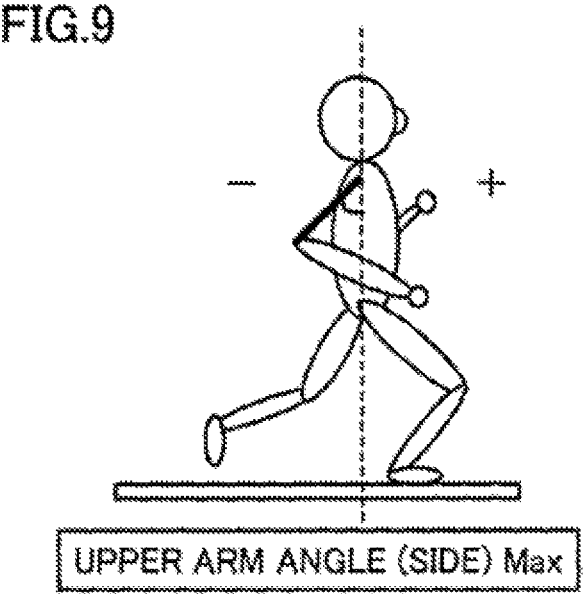
FIG. 9 is a drawing for describing "upper arm angle (side) Max" as an example of biomechanics data.

FIG. 9 is a drawing for describing "upper arm angle (side) Max" as an example of biomechanics data. The "upper arm angle (side) Max" is extracted based on an angle of the upper arm with respect to the reference line. More specifically, operation expression generating unit 34 extracts from the picture data a maximum value of an angle of the upper arm with respect to the reference line in each cycle within a certain period of time, and calculates an average value of extracted maximum values for a plurality of cycles to obtain the "upper arm angle (side) Max."

Figure 10:
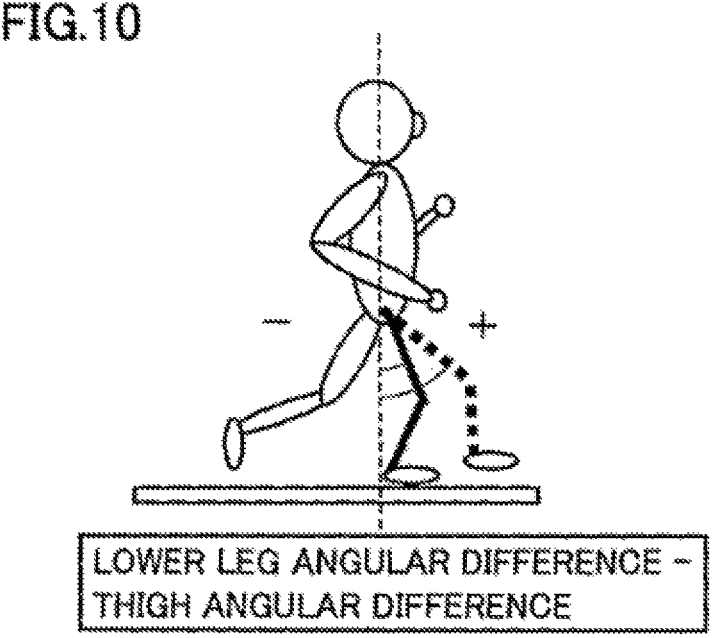
FIG. 10 is a drawing for describing "lower leg angular difference—thigh angular difference" as an example of biomechanics data.

FIG. 10 is a drawing for describing "lower leg angular difference—thigh angular difference" as an example of biomechanics data. Operation expression generating unit 34 obtains from the picture data a maximum value and a minimum value of a lower leg angle for each cycle within a certain period of time, calculates average values of the obtained maximum values and minimum values, and calculates a difference between the average value of the maximum value and the average value of the minimum value. Further, operation expression generating unit 34 obtains from the picture data a maximum value and a minimum value of a thigh angle for each cycle within a certain period of time, calculates average values of the obtained maximum values and minimum values, and calculates a difference between the average value of the maximum values and the average value of the minimum values. Then, a difference between the average value difference as to the lower leg angle and the average value difference as to the thigh angle is calculated, so that the "lower leg angular difference—thigh angular difference" is obtained.

Figure 11:
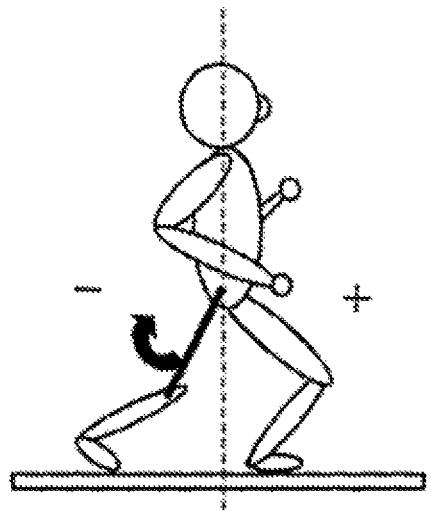
FIG. 11 is a drawing for describing "thigh angular velocity (side) Min" as an example of biomechanics data.

FIG. 11 is a drawing for describing "thigh angular velocity (side) Min" as an example of biomechanics data. Operation expression generating unit 34 extracts from picture data an angular velocity of the thigh for each cycle, calculates a minimum value of the angular velocity, and calculates an average value of minimum values for a plurality of cycles to obtain the "thigh angular velocity (side) Min."

Figure 12:
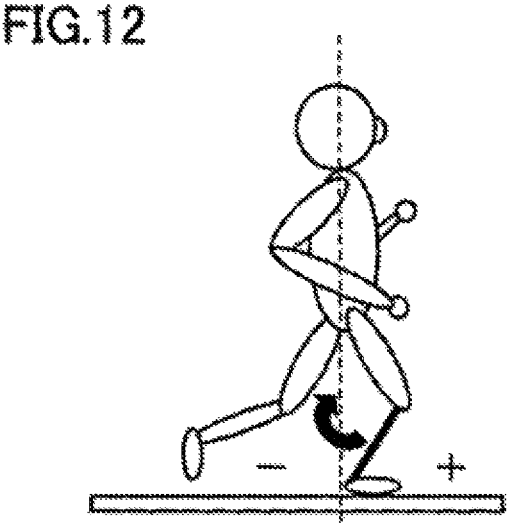
FIG. 12 is a drawing for describing "lower leg angular velocity (ground)" as an example of biomechanics data.

FIG. 12 is a drawing for describing "lower leg angular velocity (ground)" as an example of biomechanics data. Operation expression generating unit 34 extracts from the picture data an angular velocity of the lower leg at the time of grounding of the right foot for each cycle within a certain period of time, and calculates an average value of extracted angular velocitys of the lower leg for a plurality of cycles to obtain the "lower leg angular velocity (ground)."

Figure 13:
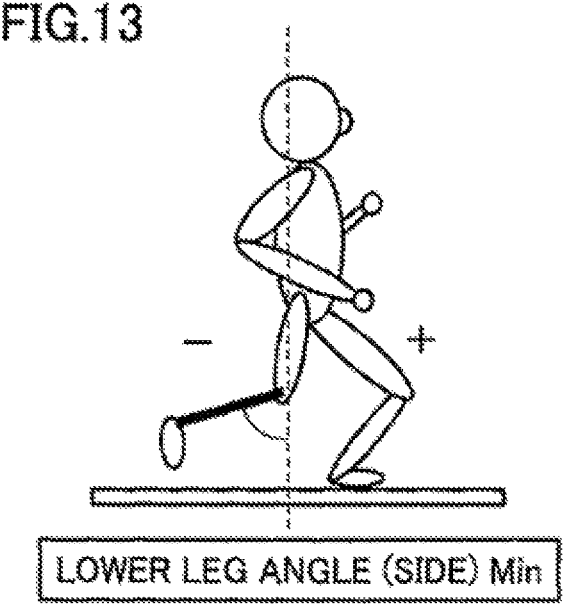
FIG. 13 is a drawing for describing "lower leg angle (side) Min" as an example of biomechanics data.

FIG. 13 is a drawing for describing "lower leg angle (side) Min" as an example of biomechanics data. Operation expression generating unit 34 extracts from the picture data a minimum value of the lower leg angle for each cycle for a certain period of time, and calculates an average value of extracted lower leg angles for a plurality of cycles to obtain the "lower leg angle (side) Min."

Figure 14:
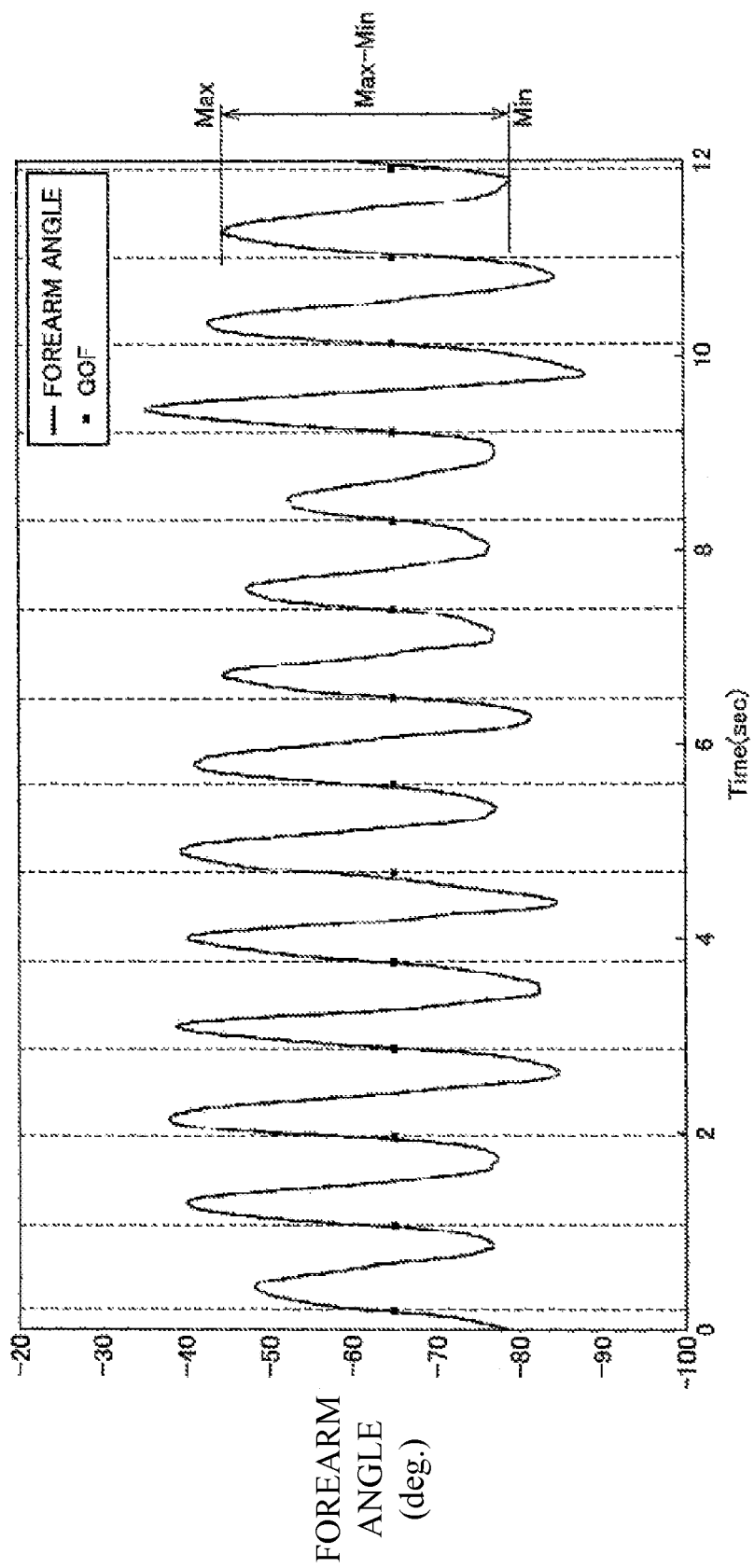
FIG. 14 represents an example of time-series data of the forearm angle.

Referring to FIG. 14, a specific example of the biomechanics data will be described. FIG. 14 represents an example of time-series data of the forearm angle. Biomechanics data extracting unit 33 generates time-series data of the forearm angle based on tracks of markers 90 in the running picture. In FIG. 14, the broken lines indicate timings of grounding of the right foot. FIG. 14 indicates twelve-seconds data. The data includes data for thirteen cycles. Operation expression generating unit 34 extracts the data shown in FIG. 14 from the picture data and further extracts a maximum value and a minimum value of the forearm angle for each cycle. Then, operation expression generating unit 34 calculates an average value of obtained maximum values and an average value of obtained minimum values for a plurality of cycles and calculates a difference between the average values to obtain the "forearm angle (side) MaxMin." In FIG. 14, the maximum value of the forearm angle at the thirteenth cycle is denoted by "Max" and the minimum value is denoted by "Min," and the difference between these values is denoted by "Max—Min."

Referring back to FIG. 5, after the biomechanics data is extracted in Step S402, operation expression generating unit 34 extracts, in Step S403, characteristics highly correlated with the running form scores given to the test runners from the user characteristics. The "user characteristics" include body characteristics of each runner (for example, BMI) and biomechanics data described with reference to FIGS. 7-14. Operation expression generating unit 34 extracts characteristics highly correlated with the running form score given to the test runner from among the characteristics of the test runner ("BMI," "thigh angle (rear) MaxMin," "forearm angle (side) MaxMin," "upper arm angle (side) Max," "lower leg angular difference—thigh angular difference," "thigh angular velocity (side) Min," "lower leg angular velocity (ground)," and "lower leg angle (side) Min"). The extraction of the highly correlated characteristics is achieved by extracting characteristics having a correlation function value greater than or equal to a certain value.

Next, operation expression generating unit 34 performs, in Step S404, a single regression analysis to generate a regression expression representing a relationship between each characteristic and a running form score. In the single regression analysis, each characteristic extracted in Step S403 is set as an explanatory variable, and the running form score is set as an objective variable.

Figures 15, 16:
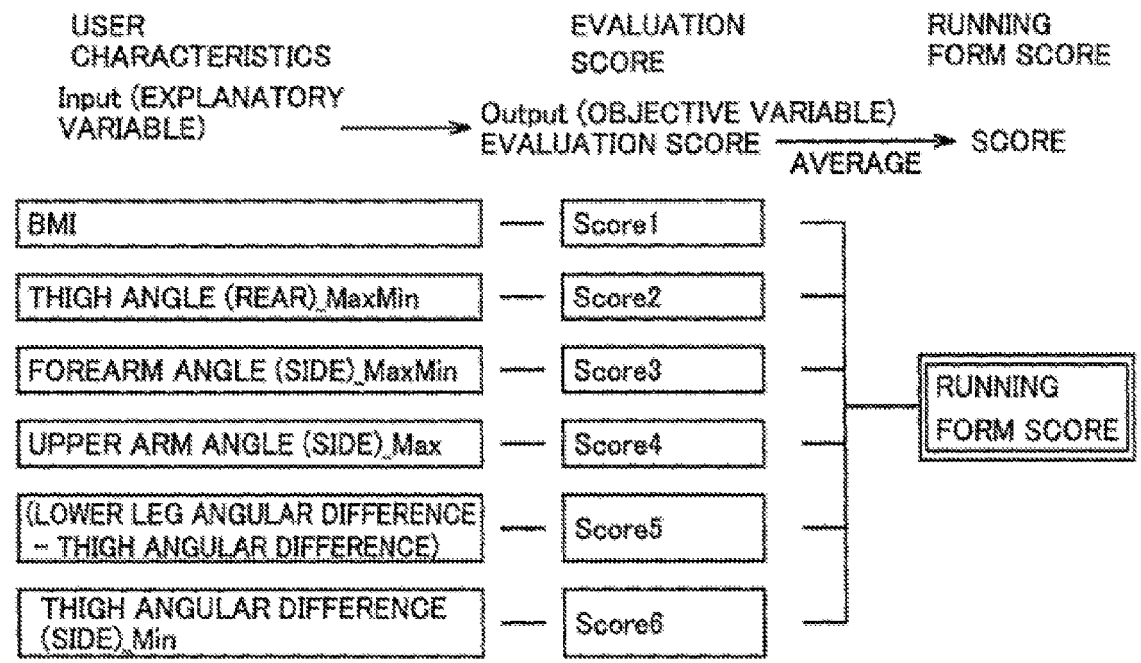
FIG. 15 represents an example of a generated regression expression.
FIG. 16 is a drawing for describing an outline of calculating a running form score using the operation expression.

FIG. 15 represents an example of the regression expression generated in Step S404. FIG. 15 represents respective regression expressions for "BMI," "thigh angle (rear) Max-Min," "forearm angle (side) MaxMin," "upper arm angle (side) Max," "lower leg angular difference—thigh angular difference," and "thigh angular velocity (side) Min" as Expressions (1)-(6). The signs "N1" and "N2" in Expression (1), signs "I1" and "I2" in Expression (2), signs "J1" and "J2" in Expression (3), signs "K1" and "K2" in Expression (4), signs "L1" and "L2" in Expression (5), and signs "M1" and "M2" in Expression (6) are coefficients used in the regression expressions. The "Score 1"-"Score 6" indicate calculation results of Expressions (1)-(6), respectively.

Generation of the operation expression (Step S401-Step S404) may be performed by score computing unit 35. Score computing unit 35 generates the operation expression by executing the processing similar to the processing in operation expression generating unit 34 described above using biomechanics data of the test runner extracted in body information extracting unit 33 and/or body characteristics extracted from the user information of the test runner inputted to user information input unit 31. In this case, operation expression generating unit 34 outputs an instruction to score computing unit 35 as to how to process the biomechanics data and the body characteristics for generation of the operation expression.

[Calculation of Running Form Score]

Score computing unit 35 calculates a running form score of a test subject in Step S204, as described with reference to FIG. 3. More specifically, score computing unit 35 extracts characteristics of the test subject necessary for Expressions (1)-(6) from the user information and the running picture of the test subject. The extracted characteristics of the test subject includes the body characteristics and biomechanics data of the test subject. Since how body information extracting unit 33 (image processing unit 33a and biomechanics data extracting unit 33b) extracts biomechanics data from the running picture of the test subject is described in a manner similar to the extraction of biomechanics data of the test runners by operation expression generating unit 34 as described with reference to FIGS. 5-14, description is not repeated.

Then, score computing unit 35 applies the extracted characteristics of the test subject to Expressions (1)-(6) respectively. Accordingly, the running form scores of the test subject are calculated preliminarily as "Score 1"-"Score 6." Then, score computing unit 35 calculates an average value of the preliminarily calculated running form scores in accordance with the following Expression (av.) to obtain the running form score of the test subject. In Expression (av.), a value of the variable "i" changes among "1" to "6." The obtained running form score is outputted as a diagnosis result in Step S205 (refer to FIG. 3).

$$(\text{Running Form Score}) = (\Sigma \text{Score} i)/6 \qquad (av.)$$

[Overview]

With reference to FIG. 16, calculation of the running form score according to the present embodiment will be described. For calculation of the running score of the test subject, the operation expression is generated based on the running picture of the test runner and the running form score given by the expert with respect to running of the test runner.

The operation expression includes mathematical expressions using six characteristics (Expressions (1)-(6)) and a mathematical expression (Expression (av.)) for calculating an average value of running form scores preliminarily calculated by these mathematical expressions. The six characteristics include "BMI," "thigh angle (rear) MaxMin," "forearm angle (side) MaxMin," "upper arm angle (side) Max," "lower leg angular difference—thigh angular difference," "thigh angular velocity (side) Min," "lower leg angular velocity (ground)," and "lower leg angle (side) Min." The characteristics of the runner (test runner and test subject) used for calculation of the running form score shown in Expressions (1)-(6) are mere examples. These characteristics are examples of those selected as being highly correlated with the running form score given to the test runner, and the number and kind are not limited to those shown in Equations (1)-(6).

In the present embodiment, the characteristics of the runner used for calculation of the running form score includes body characteristics (for example, "BMI") and biomechanics data. Further, the characteristics of the runner used for calculation of the running form score may include only biomechanics data in some cases.

Figure 17:
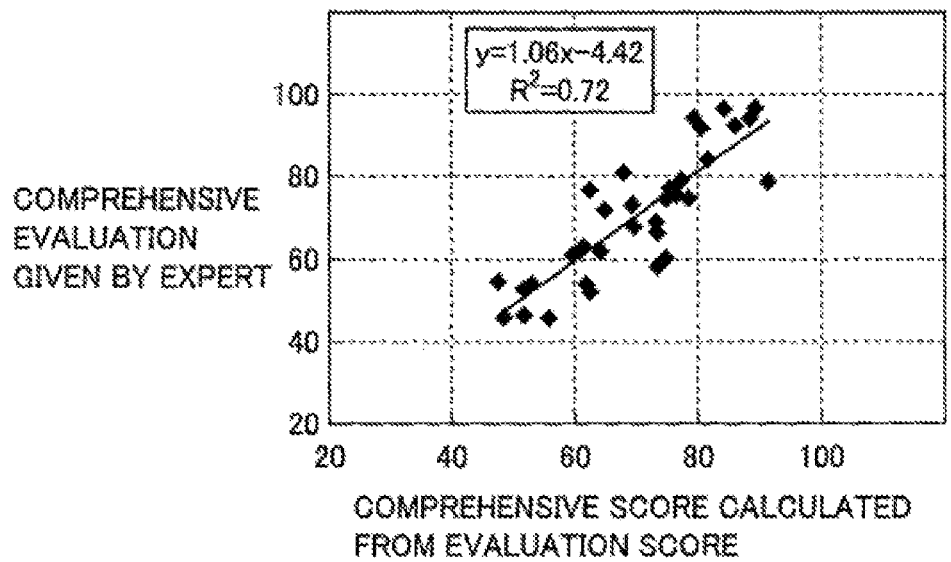
FIG. 17 represents a correlation between calculated running form scores and running form scores given by an expert.

FIG. 17 represents a correlation between running form scores calculated in accordance with the present embodiment (the running form scores calculated from the evaluation scores) and running scores given by experts for thirty-five test runners. The vertical axis of the graph in FIG. 17 represents values of the running form comprehensive evaluation given by the experts to each test runner. The horizontal axis of the graph represents values of the running form comprehensive scores calculated with use of Equations (1)-(6) and Equation (av.) based on the running picture of each test runner (the running form scores calculated from the evaluation scores).

The determination coefficient (square of multiple correlation coefficient) of the running form score given by the expert and the score calculated from the evaluation score based on the result shown in FIG. 17 was "0.74." Therefore, the method for calculating a running form score in accordance with the present embodiment can provide a score close to the running form score given by the experts in the evaluation result.

[Modified Example]

A modified example of the operation expression used for calculating the running form score and calculation of the running score using the operation expression will be described. The following description of the present modified example is mainly about the changes with respect to the running form diagnosis system shown in FIG. 1 and the like.

In the modified example, the expert gives evaluation on two or more items with respect to running of the test runner in addition to the running form score. The operation expression of this modified example includes a mathematical expression (first regression expression) associating the evaluation item highly correlated with the running form score to the running form score and a mathematical expression (second regression expression) associating the runner characteristics highly correlated with the evaluation item to the evaluation item. These mathematical expressions are generated using the body characteristics and/or running picture of the test runner.

Calculation of the running form score in this modified example includes extracting user characteristics necessary for the second regression expression from the body characteristics and/or running picture of the test subject, calculating a value of "highly correlated evaluation item" by applying the extracted user characteristics to the second regression expression, and applying the calculated value of the "highly correlated evaluation item" to the first regression expression.

Figure 18:
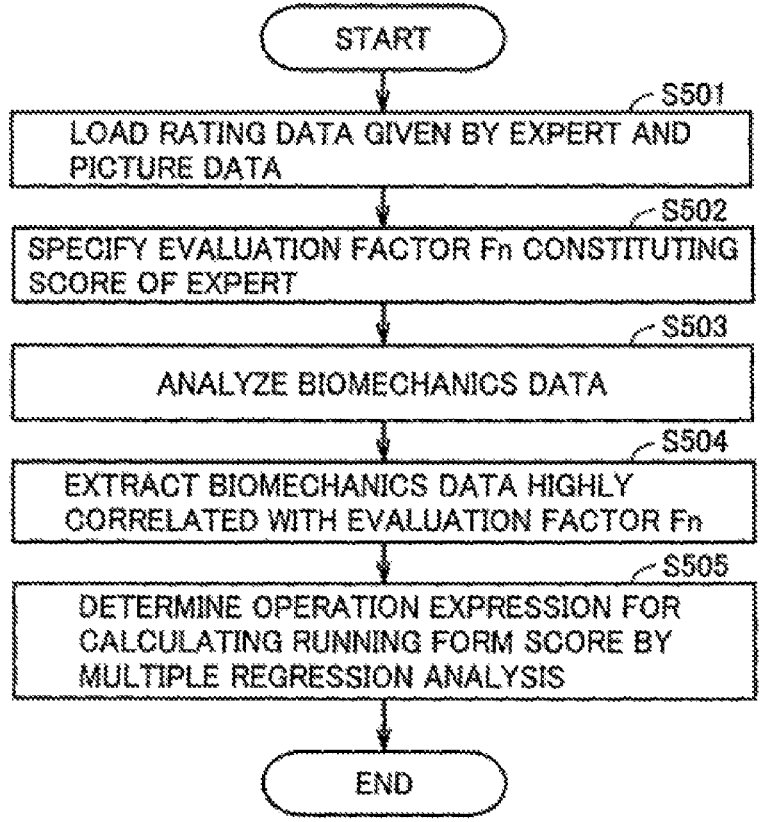
FIG. 18 is a flowchart representing a modified example of the generation of an operation expression described with reference to FIG. 5.

FIG. 18 is a flowchart representing generation of the operation expression according to the present modified example.

Referring to FIG. 18, operation expression generating unit 34 loads rating data of a questionnaire given by the N number of experts with respect to running of the M number of test runners and running pictures of the M number of test runners (Step S501). Further, in Step S501, operation expression generating unit 34 also receives an input of body information including height and weight of each test runner. As will be described later with reference to FIG. 22, the rating data includes a comprehensive running form score ("comprehensive evaluation" in FIG. 22) with respect to running of the test runner and scores of two or more skill elements ("SKILL ELEMENT 1"-"SKILL ELEMENT n" in FIG. 22) which are points for evaluating running. Each of the two or more skill elements may be identified as "skill element Fn" in the following description.

Next, operation expression generating unit 34 performs a statistical analysis on rating data of each skill element to specify skill elements Fn constituting comprehensive evaluation of a running form given by the expert (degree of achieving ideal running) (Step S502). More specifically, operation expression generating unit 34, for example, performs a factor analysis with respect to rating items (skill element and comprehensive evaluation) given by the expert in the questionnaire to group skill elements Fn into a plurality of groups of components (factors). Next, operation expression generating unit 34 specifies a correlation between the factors extracted by the grouping and the comprehensive evaluation. Then, operation expression generating unit 34 specifies a representative factor from skill elements Fn included in each factor. Operation expression generating unit 34 obtains skill elements Fn constituting the comprehensive evaluation as the specified representative factors. Accordingly, the comprehensive evaluation of the running form can be associated with specified skill elements Fn. The term "constituting" the comprehensive evaluation means "affecting greatly" on the comprehensive evaluation.

Next, operation expression generating unit 34 calculates biomechanics data of each test runner from 3D coordinate information obtained from a running picture of each test runner (Step S503). Operation expression generating unit 34 can extract biomechanics data using functions of image processing unit 33a and biomechanics data extracting unit 33b. Since how the biomechanics data is extracted is described in a manner similar to the description with reference to FIGS. 6-13, the description is not repeated.

Next, operation expression generating unit 34 finds correlation matrices as to user characteristics (extracted biomechanics data and body characteristics) and skill elements Fn specified in Step S502 (skill elements Fn constituting comprehensive evaluation) to extract user characteristics highly correlated with skill element Fn constituting the comprehensive evaluation (Step S504). The user characteristics extracted in this stage will be suitably described as parameter Xn (X1, X2, . . . Xn) in the following description.

Next, operation expression generating unit 34, in Step S505, performs the multiple regression analysis, with the scores of skill elements Fn constituting the comprehensive evaluation (scores described in the questionnaire) given by the expert as an objective variable and with extracted user characteristics Xn (body characteristics and biomechanics parameter) as an explanatory variable, to create a regression expression f2 (second regression expression) for estimating scores of skill elements Fn constituting the comprehensive evaluation from user characteristics Xn (body characteristics and biomechanics parameters). As regression expression f2, a single regression expression or a multiple regression expression is used. Further, operation expression generating unit 34, in Step S505, performs the multiple regression analysis to create a multiple regression expression f1 (first regression expression) for calculating the comprehensive evaluation (running form score) using skill elements Fn constituting the comprehensive evaluation. In the multiple regression analysis, the comprehensive evaluation is set to be an objective variable, and the score of skill element Fn constituting the comprehensive evaluation is an explanatory variable.

In the present modified example, the "operation expression" for calculating the running score of the test subject includes multiple regression expression f2 and multiple regression expression f1. Multiple regression expression f2 and multiple regression expression f1 associate the user characteristics with the running form score (comprehensive evaluation).

In the present modified example, score computing unit 35, in Step S205, applies the user characteristics generated as described above to multiple regression expression f2 to obtain a value of "highly correlated evaluation item" and further calculates a running form score by applying the value of "highly correlated evaluation item" to multiple regression expression f1.

When the evaluation described in the questionnaire is rated by multilevel evaluation, the value included in the evaluation may be displayed after being standardized in a desired score scale.

Figure 19:
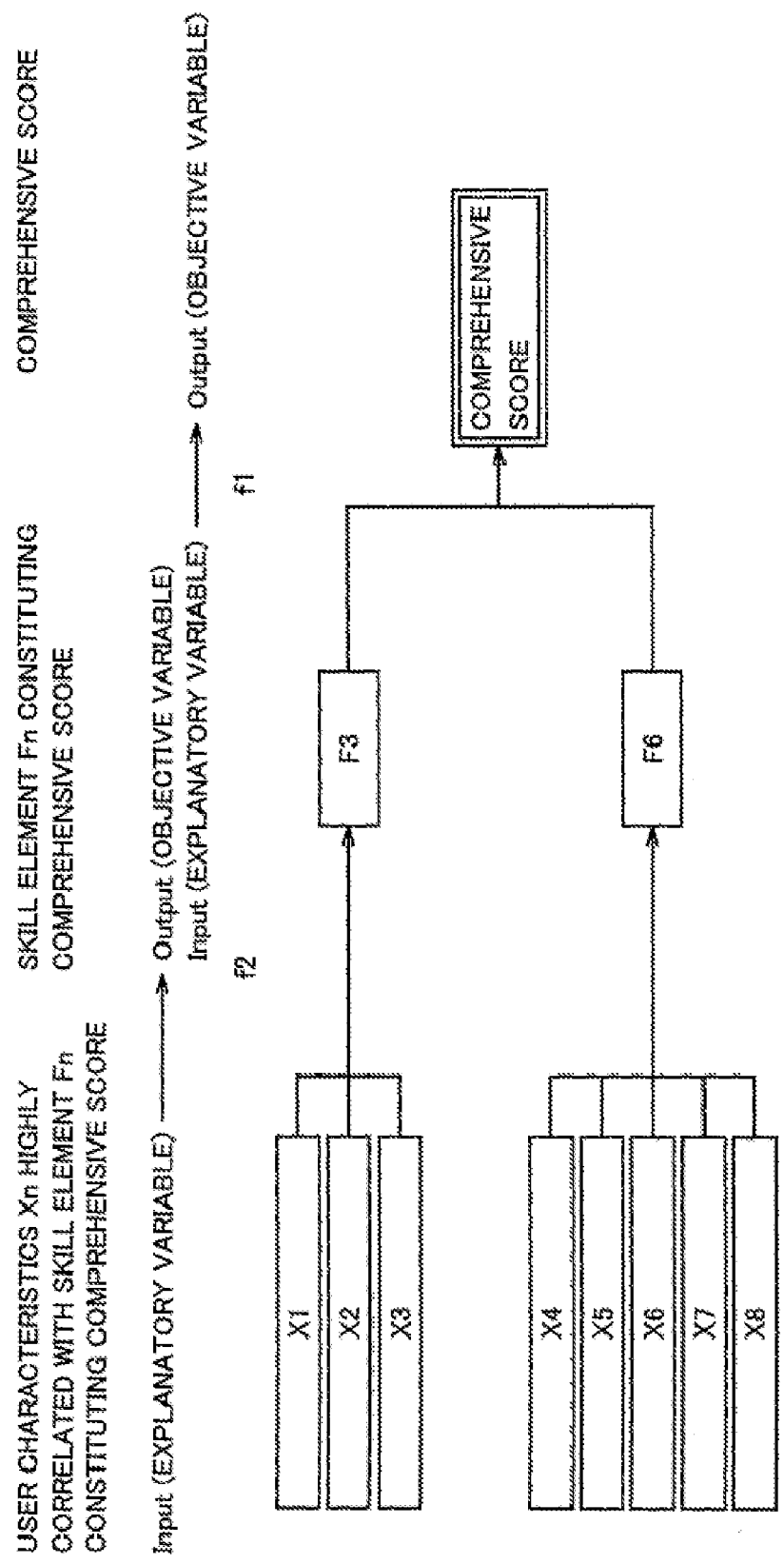
FIG. 19 represents an example of a flow of calculating a running form score.

A series of flow for calculating the running form score is shown in FIG. 19. In FIG. 19, an example is shown where skill elements F3 and F6 are obtained from skill elements Fn as skill elements constituting the comprehensive evaluation. Further, in the example, the user characteristics X1-X3 highly correlated with skill element F3 and user characteristics X4-X8 highly correlated with skill element F6 are extracted from a plurality of user characteristics. The scores of skill elements F3 and F6 are found using regression expression f1. The running form score (comprehensive evaluation) is found using regression expression f2.

Figure 20:
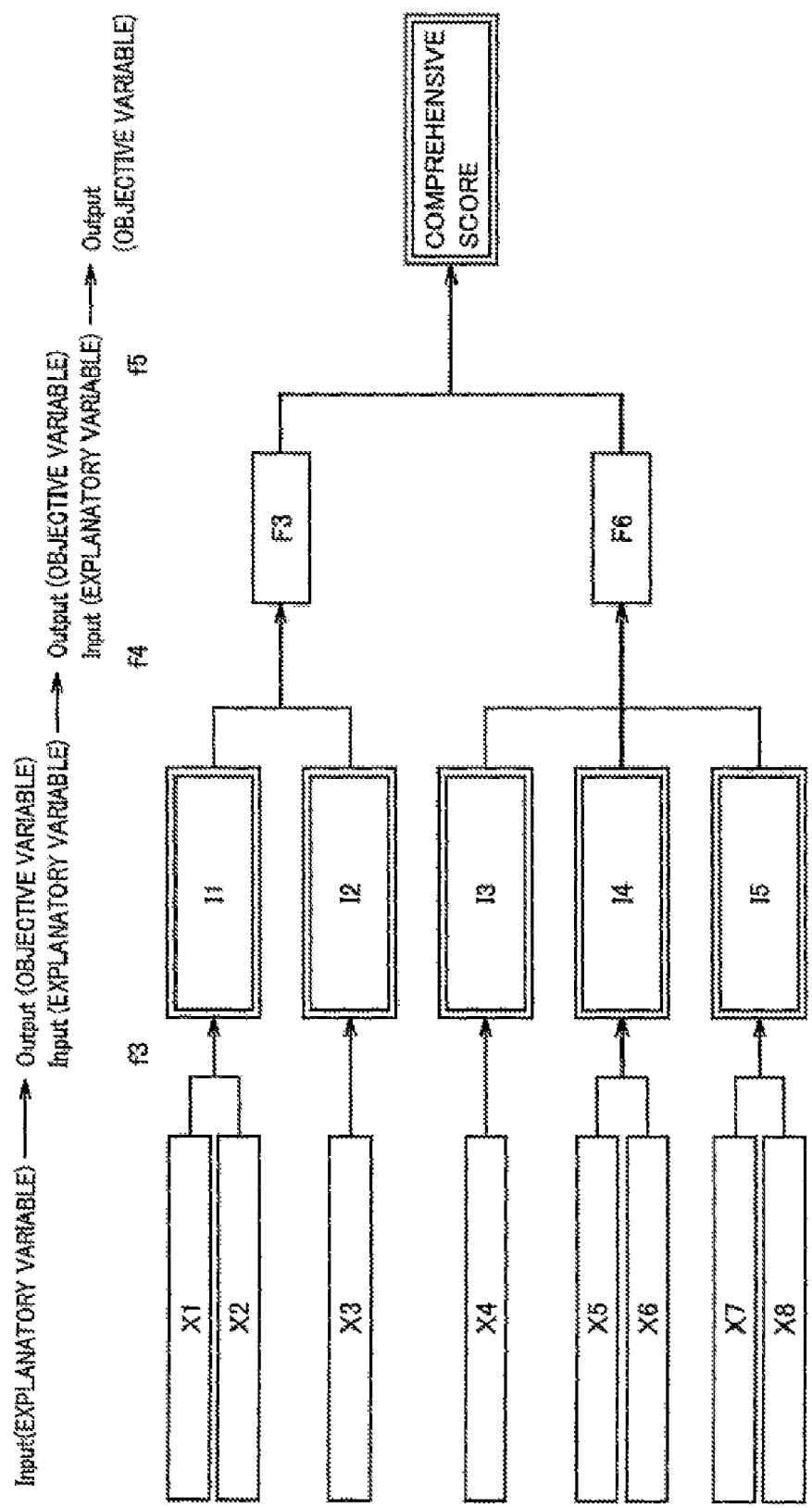
FIG. 20 represents another example of a flow of calculating a running form score.

Further, as another example, there may be a case where scores of individual evaluation items (In) of a running form is once found using parameters Xn extracted as shown in FIG. 20, and scores of skill elements Fn constituting the comprehensive evaluation are found using the scores of individual evaluation items (In), and the comprehensive evaluation is found using the scores of skill elements Fn. Any item which can be derived using parameters Xn used for calculating skill elements Fn constituting the comprehensive evaluation may be set as the individual evaluation items (In).

A series of flow for calculating the comprehensive evaluation and the scores of individual evaluation item (In) is shown in FIG. 20. In FIG. 20, the case is shown where skill elements F3 and F6 are obtained from skill elements Fn as skill elements constituting the comprehensive evaluation, and characteristics X1-X3 highly correlated with skill element F3 and characteristics X4-X8 highly correlated with skill element F6 are extracted from a plurality of user characteristics.

Further, in the example of FIG. 20, individual evaluation item I1 associable with parameters X1 and X2, and individual evaluation item I2 associable with parameter X3 are set, so that a score of skill element F3 is calculated based on the scores of individual evaluation items I1 and I2. Similarly, individual evaluation item I3 associable with parameter X4, individual evaluation item I4 associable with parameters X5 and X6, and individual evaluation item I5 associable with parameters X7 and X8 are set, so that a score of skill element F6 is calculated based on these individual evaluation items I3-I5. Then, the comprehensive score is calculated based on the scores of skill elements F3 and F6.

The scores of individual evaluation items I1-I5 are found using regression expression f3. The scores of skill elements F3 and F6 are found using regression expression f4. The running form score (comprehensive score) is found using regression expression f5.

As described above, in addition to the comprehensive evaluation point of the running form, the individual evaluation item is also scored based on the evaluation result of the expert, so that a form diagnosis for the test subject can be performed more in detail.

Figure 21:
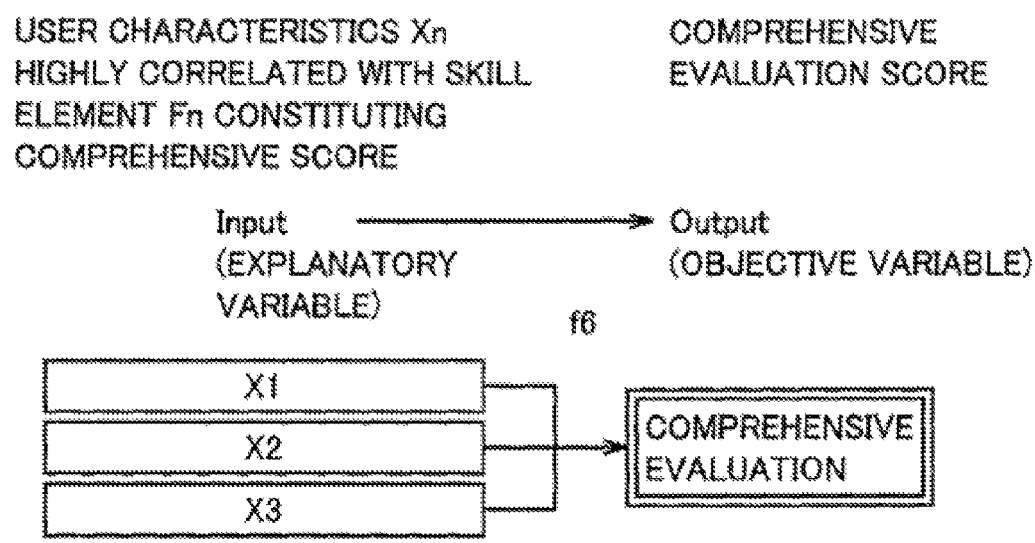
FIG. 21 represents yet another example of a flow of calculating a running form score.

Further, the multiple regression analysis, with the biomechanics data (body motion information) of the plurality of test runners as an explanatory variable and with the comprehensive evaluation given by the expert with respect to running of the plurality of test runners as an objective variable, allows the multiple regression expression for calculating a running form score directly from the body motion information of the test subject to be generated. As described above, a series of flow for calculating the running form score of the test subject is shown in FIG. 21. Further, the following Expression (X) is an example of the multiple regression expression.

$$\text{Comprehensive Score} = N1 + N2 \times \text{thigh angle (rear) MaxMin} + \\ N3 \times \text{upper arm angle (side) MaxMin} + \\ N4 \times \text{forearm angle (side) MaxMin} \quad (X)$$

According to the example shown in FIG. 21, three kinds of body motion information used for the multiple regression analysis are indicated as X1, X2, and X3. According to the multiple regression expression, as a specific example of the three kinds of body motion information, "thigh angle (rear) MaxMin," "upper arm angle (side) MaxMin," and "forearm angle (side) MaxMin" are employed.

According to the example shown in FIG. 21 and Expression (X), the number of body motion information used for the multiple regression analysis is "three." However, this is a mere example, and the number is not limited to three.

Also in the present modified example, the functional block diagram shown in FIG. 4 is applied. Running form evaluation expressions (multiple regression expressions f2, f1) are stored in a storage area (not illustrated) in operation expression generating unit 34, and is set in score computing unit 35 provided in a subsequent stage. Score computing unit 35 selects predetermined body characteristics and biomechanics parameter Xn from biomechanics data of test subject A outputted from biomechanics data extracting unit 33b, and sequentially applies it to the running form evaluation expressions (multiple regression expression f2, f1) to calculate a running form score of test subject A (Step S506).

Figure 22:
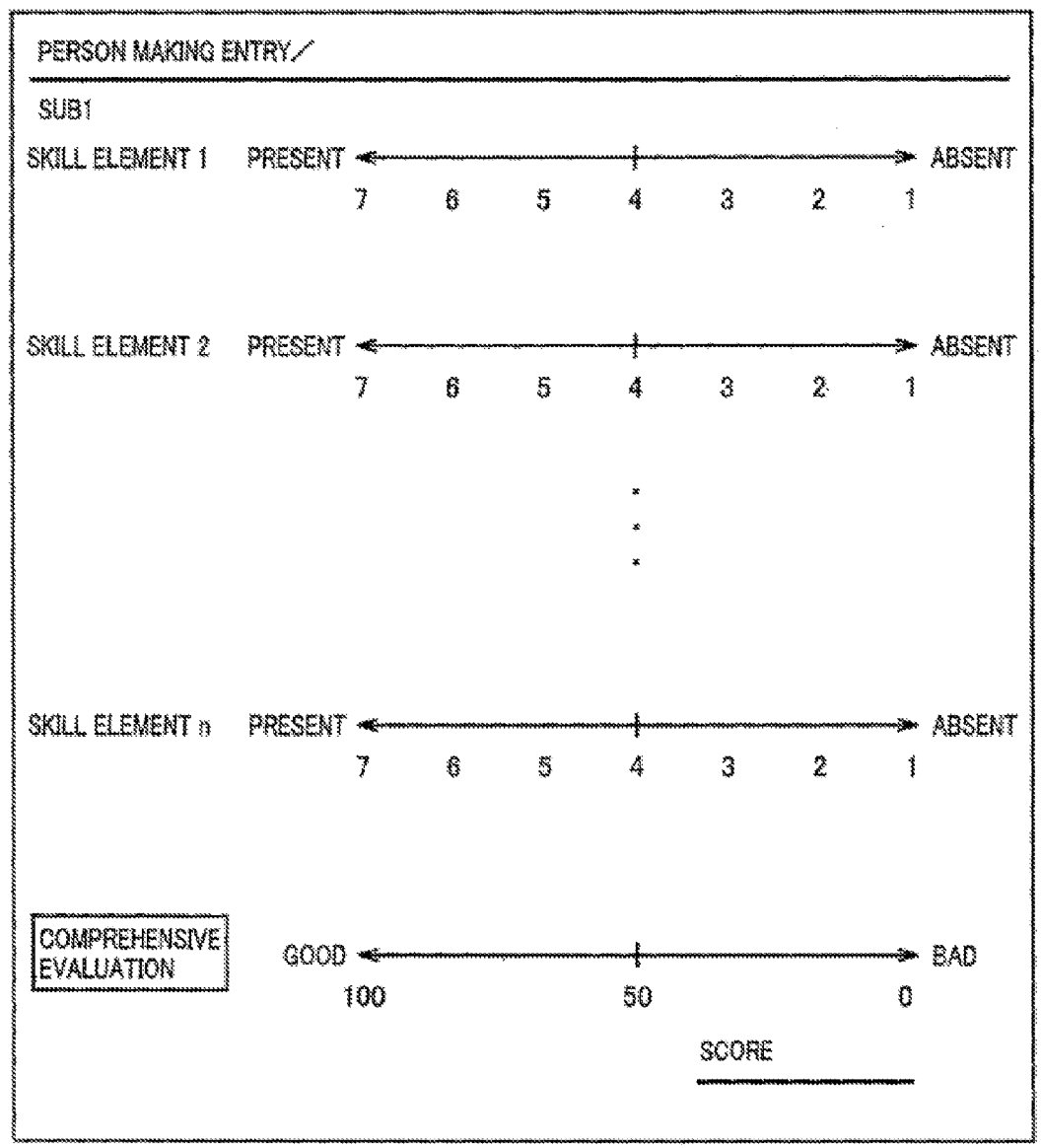
FIG. 22 represents an example of a questionnaire distributed to an expert.

With reference to FIG. 22, contents of the questionnaire used in the present modified example will be described. FIG. 22 represents an outline of the questionnaire distributed to the expert. The questionnaire includes areas for entering a rating result for each skill element ("SKILL ELEMENT 1"-"SKILL ELEMENT n" in FIG. 22) and areas for entering comprehensive evaluation (running form score) ("comprehensive evaluation" in FIG. 22).

[Example]

Hereinafter, an example of the modified example will be described. The basic configuration of the running form diagnosis system is as shown in FIG. 1. A treadmill, an image-capturing system, and analysis software used herein are as described herebelow.

Treadmill: Manufactured by Nihon Kohden Corporation

Image-capturing System: Library Co., Ltd., Giganet Image Input System GE60W (two camera spec)

Analysis Software: Library Co., Ltd., 3D moving image measuring software Move-tr/3D (including 2D software), CaptureEX (SP)

Further, six markers 90 were attached to six locations (shoulder, elbow, wrist, thigh base, knee, ankle) on the right side of a test subject.

The operation expression (running form evaluation expression) was determined based on the following process.

Firstly, running pictures of twenty runners (test runners) exhibiting different running levels were prepared. Then, twelve well-known experts watched running pictures of the twenty test runners to create rating data for each test runner. FIG. 23 represents a specific example of the questionnaire distributed to each expert.

As shown in FIG. 23, in the present example, eight items including "sense of speed," "beauty," "safeness," "sense of rhythm," "relax," "dynamism," "smooth," and "balance" were listed as skill elements, and seven-grade rating evaluation was performed. Further, a field for entering a specific score for the running form as "comprehensive evaluation" was provided.

In the questionnaire, the seven-grade rating evaluation was performed for the skill elements. However, standardization is desirable in this analysis. Therefore, the eight items of skill elements and the comprehensive evaluation may be converted to 70±15 or the like in the present example using an average and a standard variation of data for the M numbers given by the N numbers of experts.

In the following description, when each skill element itself is presented, the name of each skill element is enclosed in double quotation marks (example: "safeness" "dynamism"), and when the score of each skill element is presented, the characters "score" is attached to the end of each skill element (example: "safeness score" "dynamism score").

As a result of performing the factor analysis with respect to the rating result of the answered questionnaire, it was found that the running form score (comprehensive evaluation given by the expert) is mainly formed by "safeness score" and "dynamism score" as described below.

Figure 24:
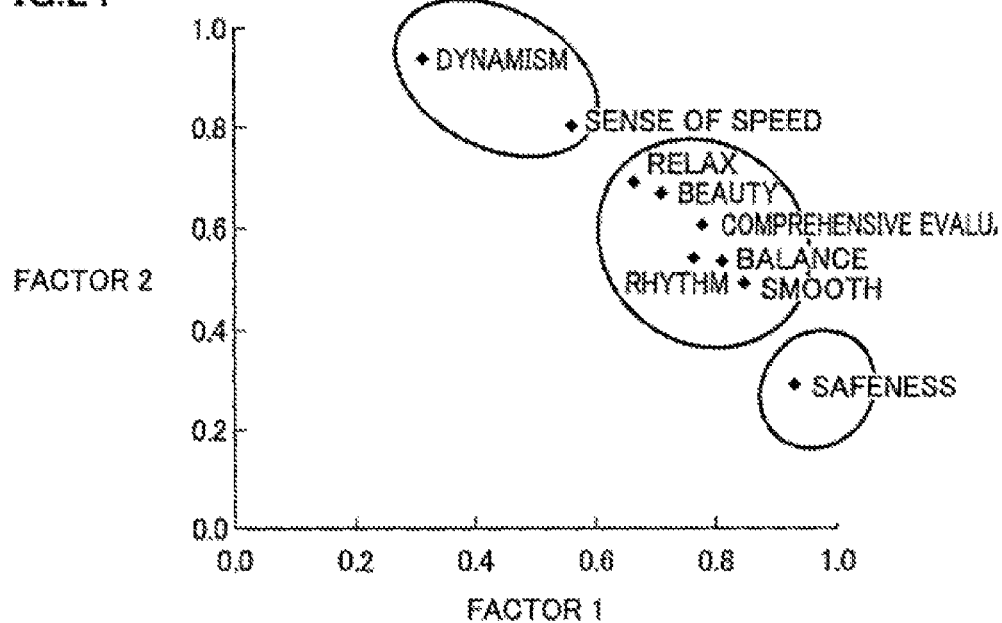
FIG. 24 plots a factor loading of each skill element with respect to a factor extracted by a factor analysis.
Figure 25:
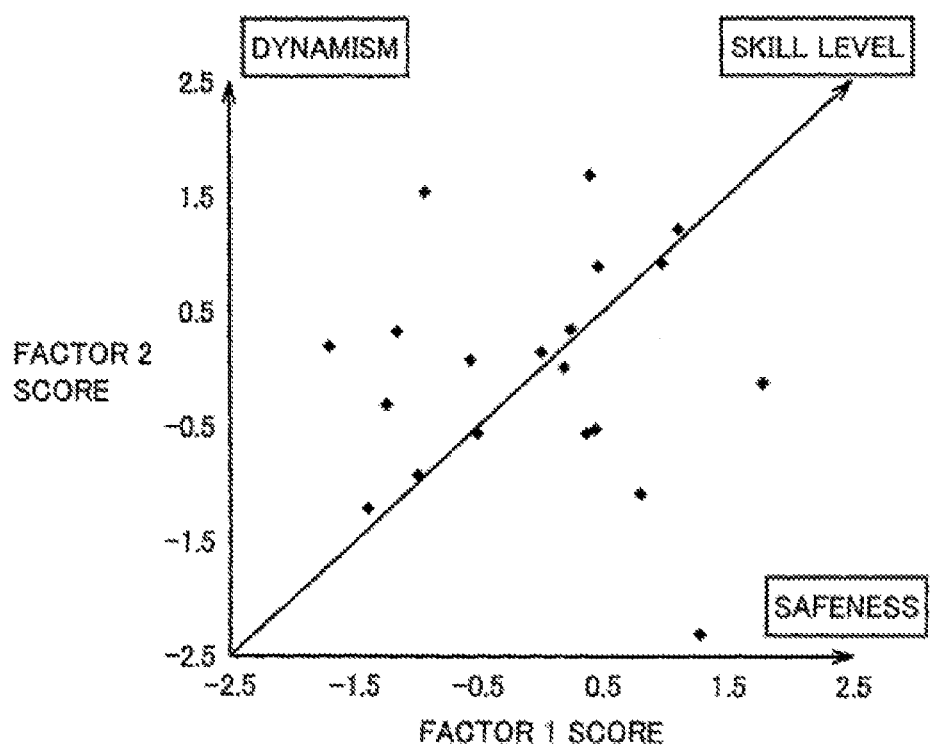
FIG. 25 plots factor scores of twenty runners.

FIG. 24 plots a factor loading of each skill element with respect to a factor extracted by the factor analysis. FIG. 25 plots factor scores of the twenty runners. Further, FIG. 26 represents a correlation between the factor scores of the extracted factors and "comprehensive evaluation."

As a result of performing the factor analysis with respect to the questionnaire evaluation items, two factors including a factor 1 and a factor 2 were extracted. After plotting the factor load of each skill element, it was found that, as shown in FIG. 24, each skill element can be grouped into a first group consisting of "dynamism" and "sense of speed," a second group consisting of "comprehensive evaluation," "beauty," "sense of rhythm," "relax," "smooth," and "balance," and a third group consisting of "safeness."

Further, as shown in FIG. 25, as a result of plotting the factor score of each skill element, it was found that the ideal running form may be grouped based on two axes of factor 1 (factor related to safeness) and factor 2 (factor related to dynamism). After making a research on a correlation between factor 1 as well as factor 2 and "comprehensive evaluation," it was found that, as shown in FIG. 26, the comprehensive evaluation of the running form given by the expert is represented by factor 1+factor 2 (score with combination of factor 1 and factor 2).

Then, as shown in FIG. 24, the "safeness score" was extracted as a representative variable from factor 1. Further, the "dynamism score" was extracted as a representative variable from factor 2. Accordingly, the comprehensive evaluation of the running form was represented by "safeness score"+"dynamism score."

Next, the user characteristics (body characteristics and/or biomechanics parameter) was extracted as respective elements for the "safeness score" and "dynamism score."

Firstly, from the running pictures of the twenty test runners, joint angles of thirty six items in total as to the fourteen joints in total including left and right hip joints, knee joints, ankle joints, sternoclavicular joints, shoulder joints, elbow joints, body trunk and neck were calculated. Further, projection angles of the body segment (thighs, lower legs, body trunk, upper torso, lower torso, upper arms, forearm, foot portions, shoulder) with respect to each plane of absolute coordinate system were calculated as body segment angles. Then, user characteristics were narrowed down by single correlation analysis and main component analysis as to a group of data including these biomechanics data with the BMI of the test subject and ground reaction data, so that user characteristics (parameter) highly correlated with "safeness score" and "dynamism score" were extracted. The narrowing down for the extraction of user characteristics were performed while avoiding multicollinearity.

As a result of the processing described above, three elements in total including "BMI" as one of the body characteristics, "thigh angle (rear) MaxMin" and "forearm angle (side) MaxMin" in the biomechanics data were extracted as user characteristics highly correlated with the "safeness score." Further, five elements in total including "upper arm angle (side) Max," "thigh angular velocity (side) Min," "lower leg angle (side) Min," "lower leg angular difference—thigh angular difference," and "lower leg angular velocity (ground)" were extracted from biomechanics data as user characteristics highly correlated with "dynamism score."

The body characteristics and biomechanics parameters extracted in relation to "safeness score" and "dynamism score" were those described with reference to FIGS. 6-13. The biomechanics data used in this stage is extracted (calculated) as described with reference to FIGS. 6-13. Extraction (calculation) of biomechanics data requires at least six markers. More specifically, the six markers are mounted to the runner's shoulder joint, elbow joint, wrist joint, base joint, knee joint, and ankle joint. Using these markers mounted on the shoulder joint, elbow joint, and wrist joint, angle information of the upper arm and forearm can be obtained. Further, using markers mounted on the base joint, knee joint, and ankle joint, angle information of the thigh and lower leg can be obtained.

Next, using the multiple regression analysis, expressions representing the evaluation items "safeness score" and "dynamism score" were constructed from the extracted user characteristics (body characteristics and biomechanics data). This means that the multiple regression expression for obtaining the evaluation point of the running form (comprehensive evaluation) were found. In the present example, in addition to the comprehensive evaluation, points (individual evaluation score) for each individual evaluation item of the running form is displayed. Each individual evaluation item was calculated based on the extracted user characteristics (body characteristics and biomechanics parameters). Then, based on each calculated individual evaluation score, the comprehensive evaluation was calculated.

FIG. 27 represents an example of a group of mathematical expressions used for calculation of the running form score in the present example. FIG. 27 represents Expressions (7)-(14).

As to the evaluation item "safeness score," the regression analysis was performed with "BMI," "thigh angle (rear) MaxMin," and "forearm angle (side) MaxMin" as an explanatory variable and with "individual evaluation score" as an objective variable. The expression for calculating the score for the individual evaluation item which can be derived with use of the above-described three parameters is specified as shown in Expressions (7) and (8) of FIG. 27. The names of the specified individual evaluation items (Safety, Relax) were set appropriately taking in consideration the corresponding skill elements.

Similarly, the expression for calculating the score of the individual evaluation item capable of defining "upper arm angle (side) Max," "thigh angular velocity (side) Min," "lower leg angle (side) Min," "lower leg angular difference—thigh angular difference," and "lower leg angular velocity (ground)" related to the evaluation item "dynamism score" as an explanatory variable was specified as shown in Expressions (10)-(13) of FIG. 27.

In FIG. 27, Expression (9) is a regression expression for calculating the "safeness score" using values calculated by Expressions (7) and (8). Expression (13) is a regression expression for calculating the "dynamism score" using values calculated by Expressions (10)-(12). Expression (14) is a regression expression for calculating a comprehensive score using the "safeness score" of Expression (9) and the "dynamism score" of Expression (13).

Figure 28:
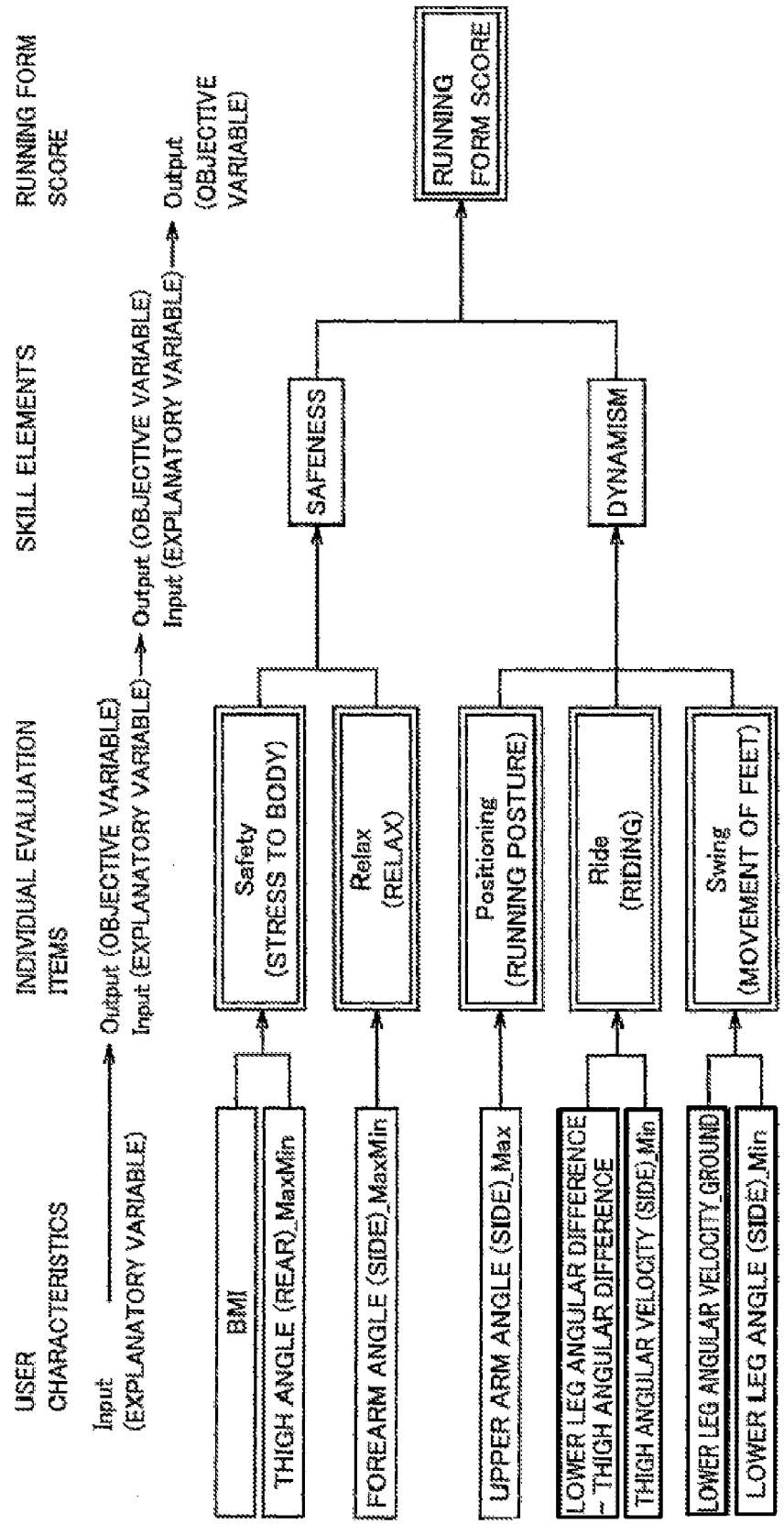
FIG. 28 represents a relationship between body characteristics as well as biomechanics parameters, evaluation items, skill elements calculated using the evaluation items, and a running form score calculated using the skill elements.

FIG. 28 represents a relationship between the body characteristics as well as biomechanics parameters extracted in a manner described above, the individual evaluation item (for determining the skill elements), the skill elements calculated with use of the individual evaluation item, and the running form score calculated with use of the skill element.

In the relationship between the skill elements and the running form score shown in FIG. 28, scores of the skill elements "safeness score" and "dynamism score" are calculated with use of the scores of calculated five individual evaluation items ("Safety," "Relax," "Positioning," "Ride," and "Swing"). Then, with use of the skill elements "safeness score" and "dynamism score," the comprehensive score (running form score) is calculated by Expression (14).

The scores of the skill elements and the comprehensive score found in the manner described above is provided on an output sheet as an evaluation result together with an advice comment of the expert prepared in advance in accordance with respective score distributions. The advice comment is selected in the manner described herebelow. In other words, the scores of the skill elements and the comprehensive score are grouped into 86 points or greater, 85-76 points, 75-56 points, and 55 points or less, and an advice for a runner in each score zone is set in advance. The contents of the advice to be set is determined based on the contents of hearing with respect to an expert. Output data creating unit 36 selects from data storage unit 32 or the like an advice comment in accordance with a score of the test subject, and provides it on the output sheet. Then, the forms of grouping (the range of scores in each group) is not limited to those described above, and another form may be employed.

Figure 29:
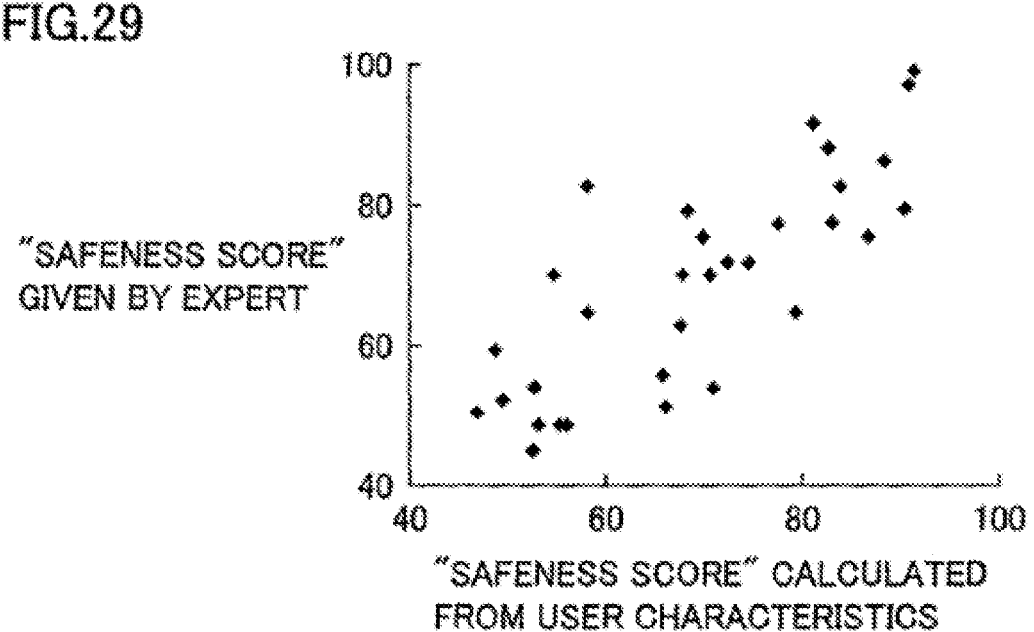
FIG. 29 represents a relationship between calculated scores and scores given by an expert, as to the skill element "safeness."
Figure 30:
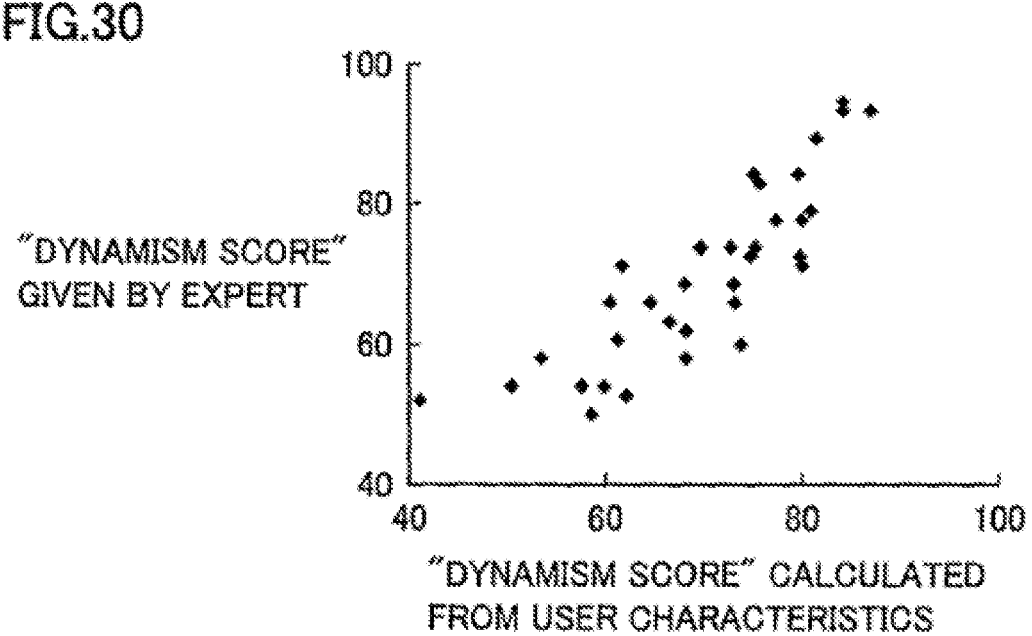
FIG. 30 represents a relationship between calculated scores and scores given by an expert, as to the skill element "dynamism."
Figure 31:
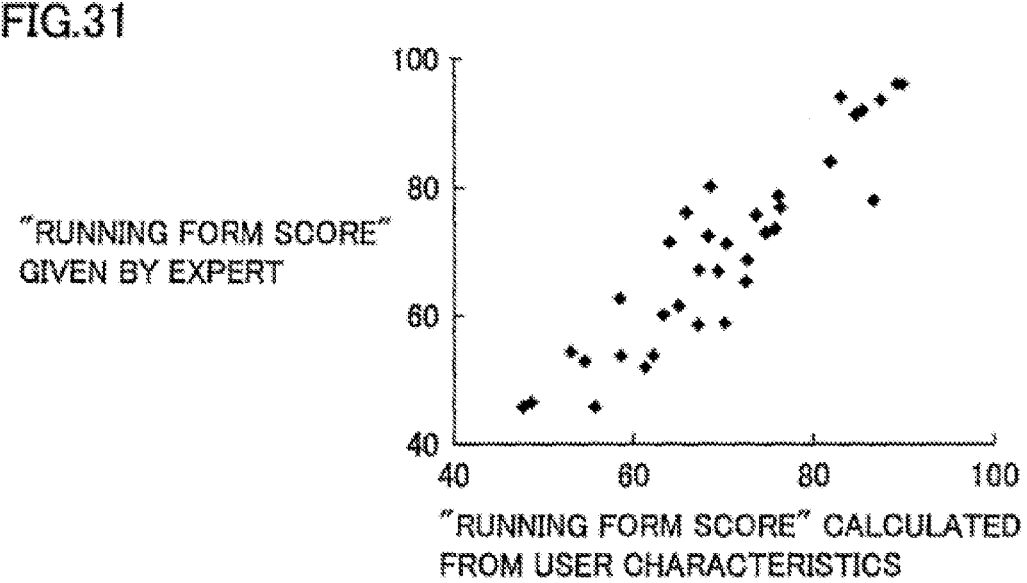
FIG. 31 represents a relationship between calculated running form scores and running form scores given by an expert.

FIGS. 29-31 represent thirty-five runners associated with the relationship between the score calculated by the running form diagnosis system of the present example and the score of the expert with respect to each runner. FIG. 29 represents a relationship of scores of the skill element "safeness." FIG. 30 represents a relationship of score of the skill element "dynamism." FIG. 31 represents a relationship of the running form scores.

As can be understood from FIGS. 29-31, with regard to all of "safeness score," "dynamism score," and "comprehensive evaluation," a high correlation is indicated between the scores of the running form diagnosis system of the present example and the evaluation of the expert. For example, in the relationship as to the running form scores, the determination coefficient for the score given by the expert and the calculated score was 0.84. Accordingly, efficacy of the accuracy in evaluation performed by the running form diagnosis system of the present embodiment was confirmed. Further, by comparing the results of FIGS. 17 and 31, it was confirmed that the accuracy of the evaluation in the modified example is higher than the accuracy of the evaluation in the present embodiment.

[Specific Example of Output Sheet]

Figure 32:
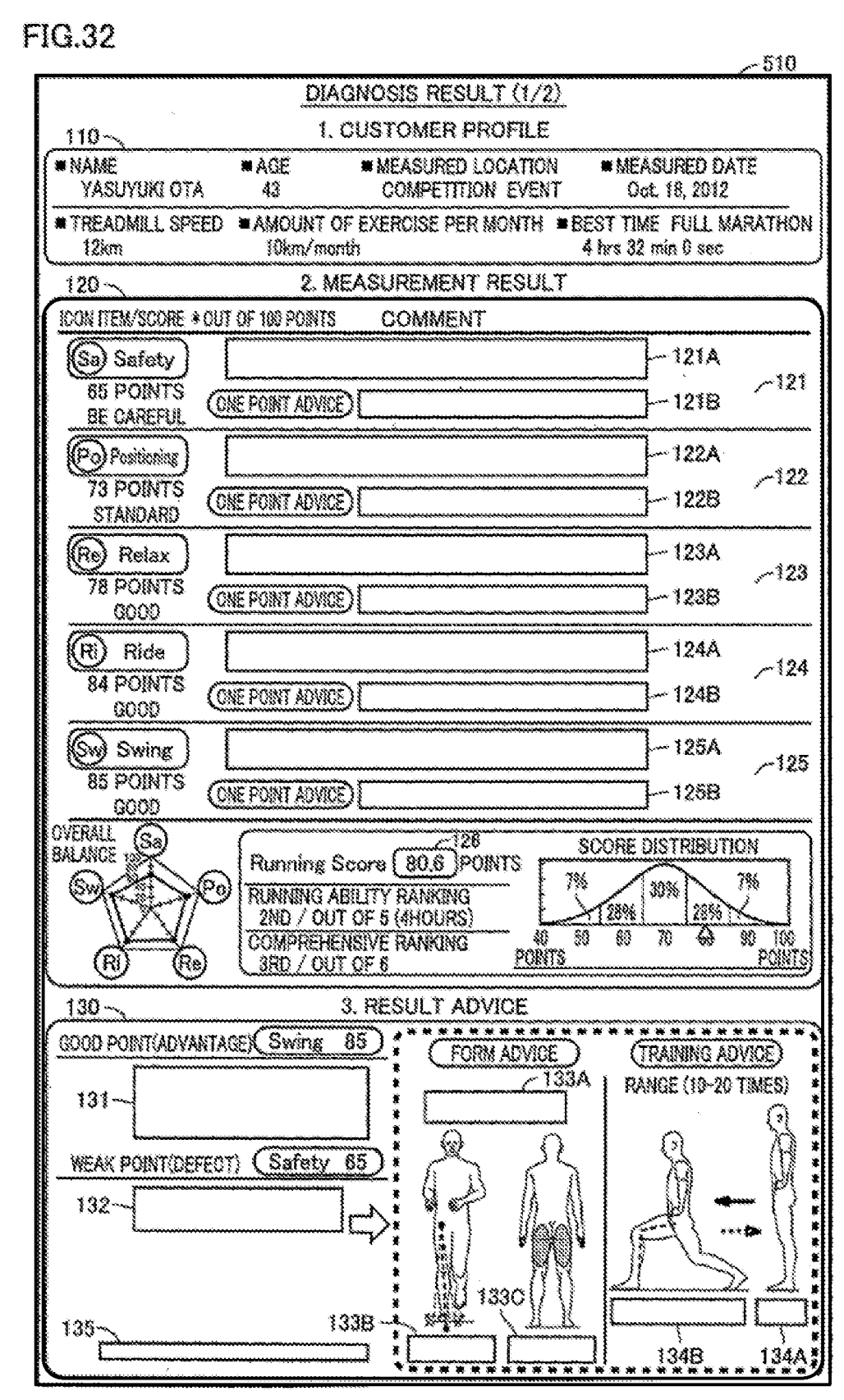
Figure 33:
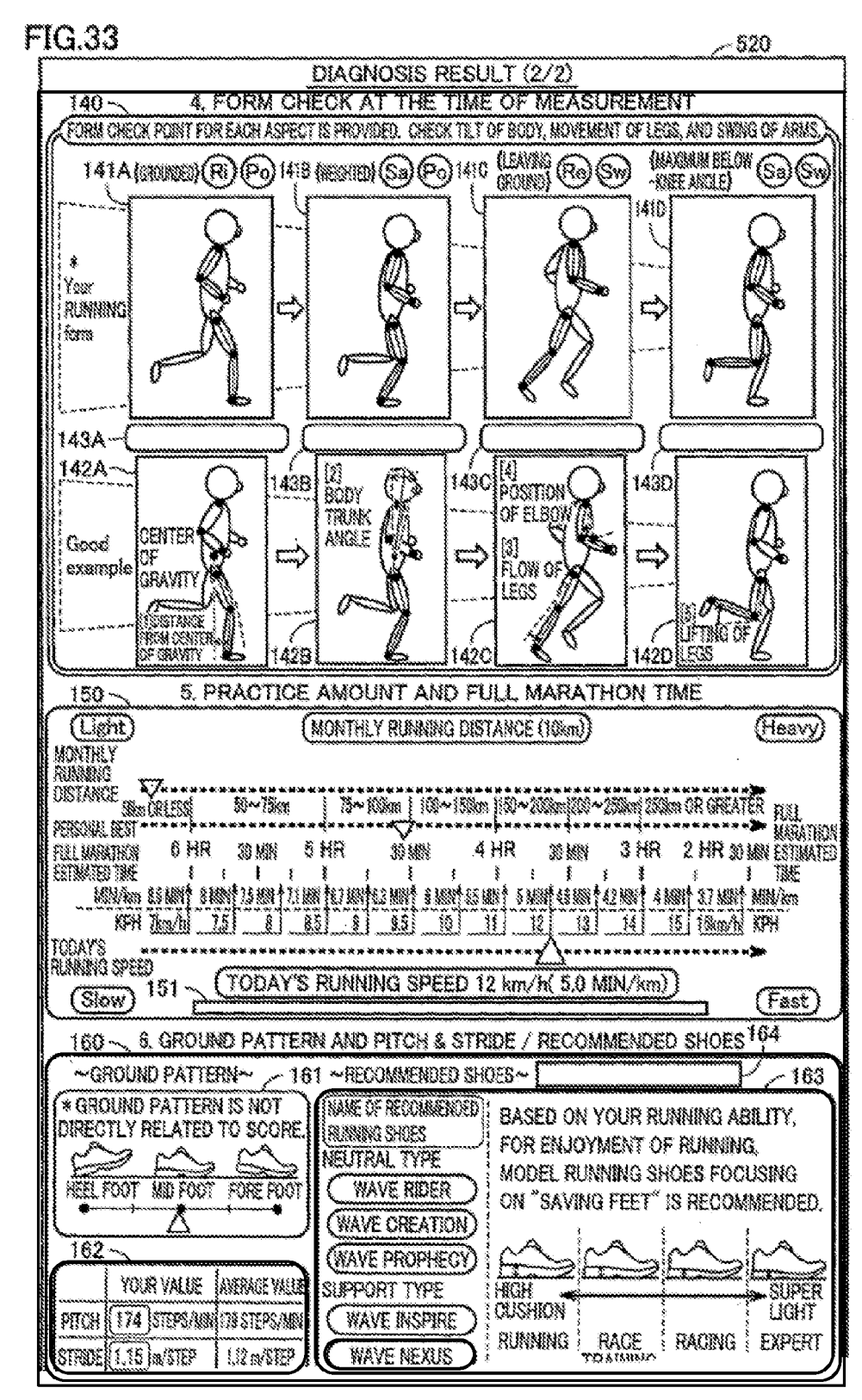

Next, a specific example of the output sheet outputted by output device 40 will be described. FIGS. 32 and 33 represent a specific example of the output sheet.

The output sheet includes a sheet 510 shown in FIG. 32 and a sheet 520 shown in FIG. 33. Sheet 510 includes a field 110 indicating a profile of a test subject, a field 120 indicating a score such as a running form score given to running of the test subject, a field 130 indicating an advice with respect to the test subject, a field 140 indicating an image of a running form of the test subject, a field 150 indicating a practice plan proposed to the test subject, and a field 160 indicating information of shoes or the like recommended to purchase with respect to the test subject. Output data creating unit 36 generates information to be provided on field 110 based on information or the like inputted to user information input unit 31.

Field 120 includes fields 121-125 for displaying respective scores of five evaluation items shown in FIG. 28 and a field 126 for displaying the running form score. Fields 121-125 respectively include fields for displaying advice comments in accordance with the scores of the evaluation items. More specifically, field 121 includes fields 121A, 121B. Field 122 includes fields 122A, 122B. Field 123 includes fields 123A, 123B. Field 124 includes fields 124A, 124B. Field 125 includes fields 125A, 125B. Data storage unit 32 stores advice comments associated with scores grouped in advance as to the scores of the evaluation items. Output data creating unit 36 selects advice comments corresponding to the scores of the evaluation items from the advice comments stored in data storage unit 32 and allows fields 121-125 to display the same.

Field 121A displays advice comments corresponding to the score of the evaluation item "Safety," the score of which is displayed in display field 121. The displayed advice comment displayed, for example, "There is a possibility of causing bothering to running if a stress to a body becomes high. Because "BMI, skeleton, muscular strength, habit in running" causes legs to waver leftward and rightward, to make higher a stress to the base joint and knee. When the loss of weight is required, run in a slow pace and continue the same. If your legs waver in leftward and rightward, pay attention to a position of grounding and direction of toes."

Data storage unit 32 stores points which should be noticed by the test subject in association with respective scores grouped in advance with regard to the score of each evaluation item. Field 121B displays points associated with the scores shown in field 121. The contents to be displayed on field 121B are, for example, [position of grounding and direction of toes], [muscle training for abdominal muscles and muscles around hip], [diet], and [select suitable shoes and supporter of one having bow-legs and knock-knees].

Under the scores displayed respectively in fields 121-125, evaluation associated with each score is displayed. The contents of the evaluation are associated respectively with the scores grouped in advance as to each evaluation item and stored in data storage unit 32. The evaluation includes, for example, the messages of "good," "standard," and "be careful" in a descending order from evaluation corresponding to higher score.

Field 130 includes, a field 131 for displaying comments on the evaluation item corresponding to the highest score among the scores shown in fields 121-125, and a field 132 for displaying comments on the evaluation item corresponding to the lowest score. Field 131 displays comments as to the evaluation item "Swing." The comments includes, for example, "Based on a result of the Swing item, kicking is performed at a good timing, and good swing is performed until grounding. Be aware of swinging legs forward quickly for further improvement." Field 132 displays comments on the evaluation item "Safety." The displayed comment includes, for example, "As a result of the Safety item, wobbling to left and right can be seen, so is unstable. Try to improve by weight control, training, and the like."

Field 130 displays "form advice" and "training advice" based on the evaluation items with the lowest scores. The "form advice" and "training advice" respectively include an image of a person to specifically present contents of the advice. Further, the "form advice" includes fields 133A-133C for displaying specific messages. The "training advice" includes fields 134A, 134B containing specific messages. Field 130 further includes a field 135 displaying cautionary words noting that the advices showing the "form advice" and "training advice" are mere examples of the considered advices.

Referring to FIG. 33, field 140 includes images 141A-141D representing a running form of the test subject, and images 142A-142D representing a running form of a model runner. Output data creating unit 36 obtains images 141A-141D from the running picture of the test subject captured by image-capturing system 20. Images 142A-142D are stored in data storage unit 32. Images 141A, 142A are images at the time of grounding. Images 141B, 142B are images at the time of being applied with weight. Images 141C, 142C are images at the time of leaving the ground. Images 141D, 142D are images at the time when the angle with respect to the perpendicular direction of the lower knee (lower leg) during running becomes maximum. Fields 143A-143D display messages indicating points which should be confirmed by the runner at the respective four points of time described above.

Field 150 displays information such as an estimated time of a full marathon calculated based on the running form score and the like of the test subject. Field 150 includes a field 151 displaying a message that the estimated time and the like displayed in field 150 is a rough indication.

Field 160 includes a field 161 indicating a grounding pattern assumed for the test subject, a field 162 indicating a measurement result of a pitch and a stride of the test subject, and a field 163 displaying information of shoes recommended to purchase for the test subject. Further, field 160 includes a field 164 indicating a message that the information of shoes presented in field 163 is schematic, and that it is recommended to actually try shoes to know more specific information about shoes fitted to the test subject.

[Extraction of Biomechanics Data Based on Measurement of Inertial Sensor]

Figure 34:
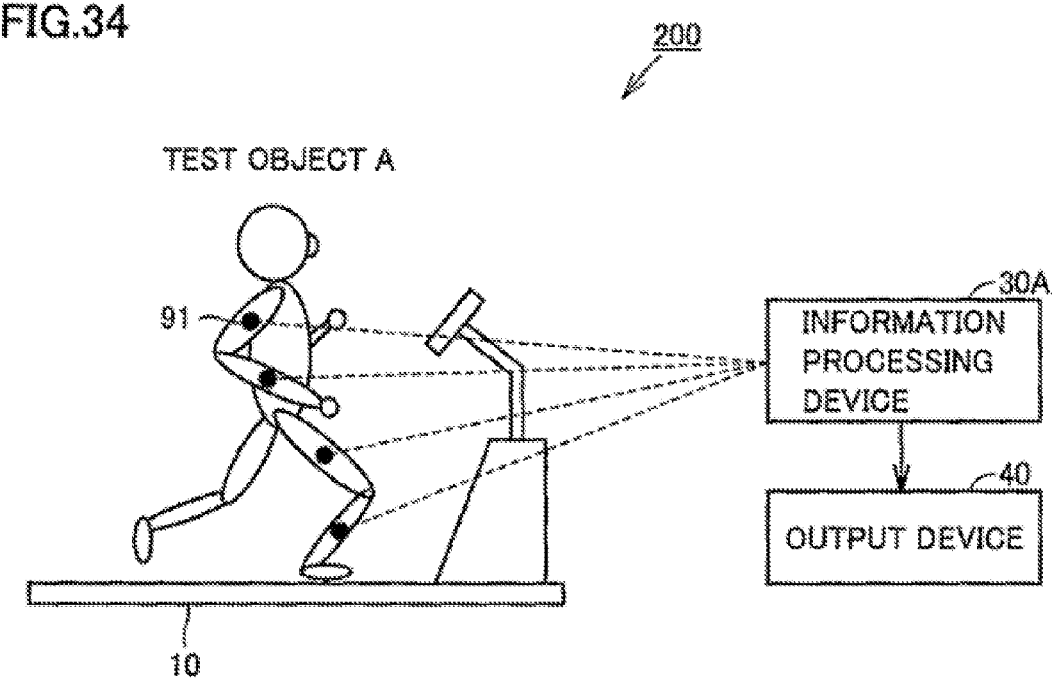
FIG. 34 represents a schematic configuration of a modified example of the running form diagnosis system.

Referring to FIG. 34, a modified example of the running form diagnosis system will be described. FIG. 34 represents a schematic configuration of the modified example of the running form diagnosis system. In the following description, the running form diagnosis system according to the present modified example will be described. The description is mainly about the points changed from the system shown in FIG. 1.

As shown in FIG. 34, in running form diagnosis system 200, the test subject running on treadmill 10 wears inertial sensors 91. The test subject wears inertial sensors 91 at two locations between which a joint whose joint angle should be measured is provided. More specifically, the test subject wears inertial sensors 91, for measurement of angles and the like of the upper arm, forearm, thigh, and lower leg, wears inertial sensors 91 respectively at the right or left upper arm portion, forearm portion, thigh portion, and lower leg portion.

The system shown in FIG. 34 includes an information processing device 30A in place of information processing device 30 shown in FIG. 1. Information processing device 30A obtains a measurement result of inertial sensors 91. Inertial sensor 91 transmits the measurement result to information processing device 30A, for example, by wireless communication. Information processing device 30A uses the measurement result obtained from inertial sensors 91 to calculate the running form scores of the test subject and outputs the same to output device 40. Output device 40 outputs the running form score.

Information processing device 30A, based on the measurement result of inertial sensor 91, calculates angle information and/or angular velocity of the upper arm, forearm, thigh, and lower leg. For example, an inertial measurement unit manufactured by Seiko Epson Corporation having functions of both gyrosensor and accelerometer is employed as inertial sensors 91. Inertial sensors 91 may measure an angular velocity and an acceleration rate as to three axial directions and output the same to information processing device 30A.

Figure 35:
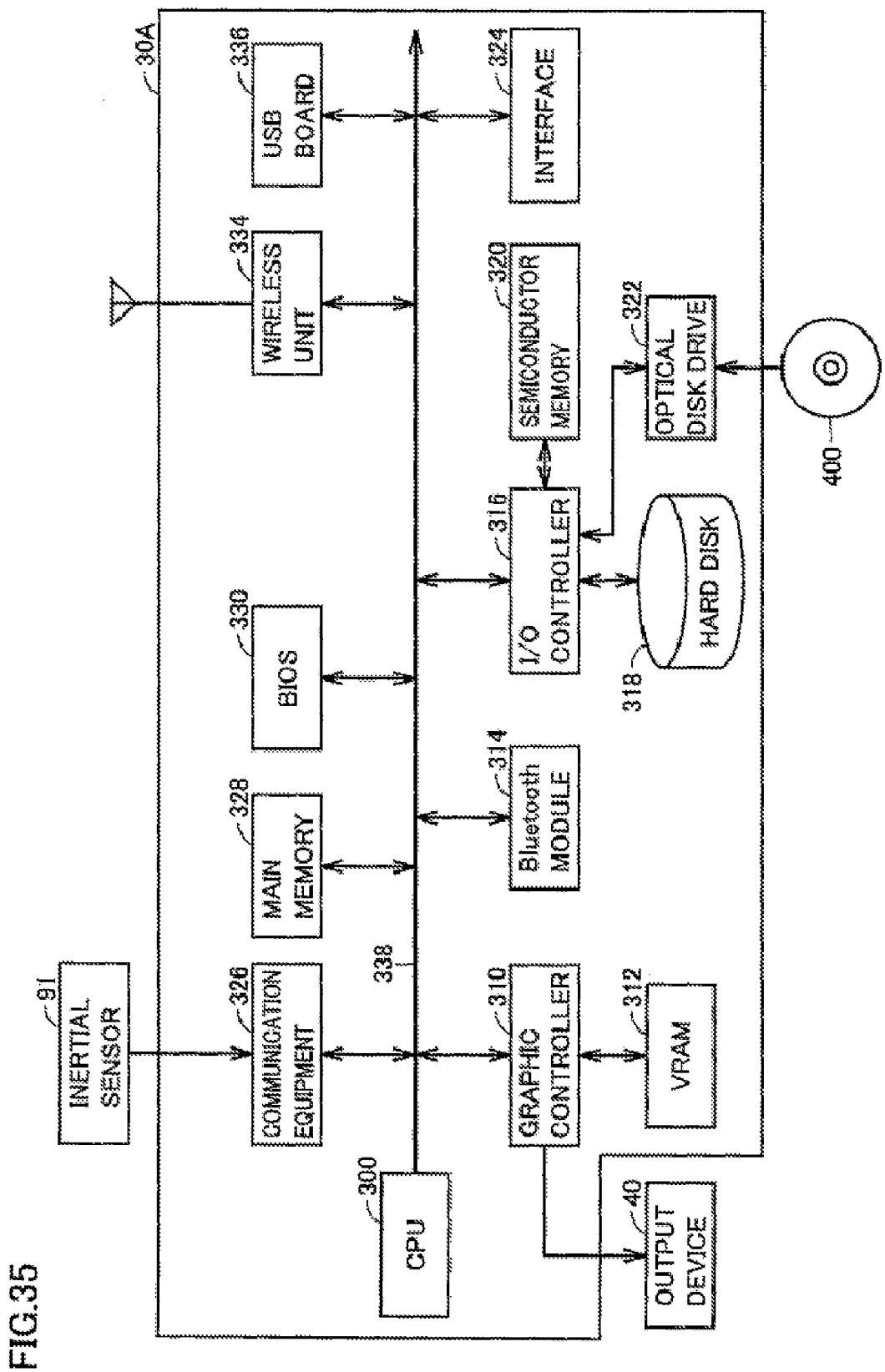
FIG. 35 represents a modified example of a hardware configuration of the information processing device.

FIG. 35 represents an example of a hardware configuration of information processing device 30A. As shown in FIG. 35, communication equipment 326 of information processing device 30A receives a measurement result transmitted from inertial sensors 91. CPU 300 processes the received measurement result to calculate a running form score of the test subject.

Figure 36:
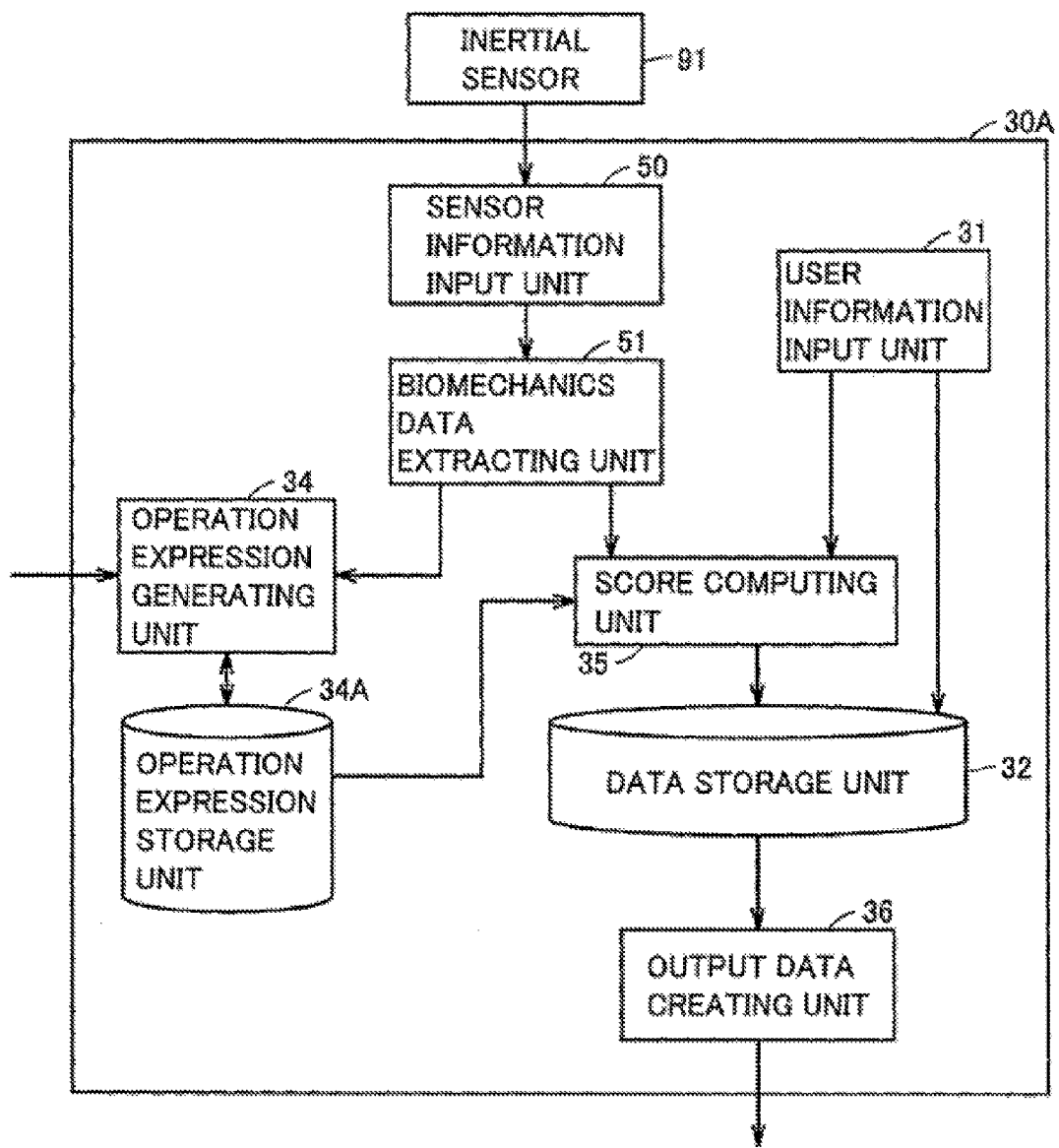
FIG. 36 represents a modified example of a functional configuration of the information processing device.

FIG. 36 represents an example of the functional configuration of information processing device 30A. Referring to FIG. 36, information processing device 30A includes a sensor information input unit 50 for receiving an input of information from inertial sensors 91. Sensor information input unit 50 is configured by, for example, communication equipment 326. Biomechanics data extracting unit 51 extracts biomechanics data of the test subject from the measurement result of inertial sensors 91. Biomechanics data extracting unit 51 is achieved, for example, by CPU 300 executing a given program.

Score computing unit 35 of information processing device 30A applies the biomechanics data and/or body information of the test subject to the operation expression generated by operation expression generating unit 34 to calculate the running form score of the test subject.

For generation of the operation expression used in information processing device 30A, the biomechanics data of the test runner is used. The biomechanics data of the test runner may be the one extracted from the measurement result of inertial sensors 91 or may be the one extracted from the images captured by image-capturing system 20 as described with reference to FIG. 1.

Running form diagnosis system 200 described with reference to FIGS. 34-36 extracts biomechanics data of the test subject from the measurement result of inertial sensors 91. Image-capturing system 20 measures the test subject from a plurality of angles. Therefore, it is estimated that the size of the device configuration becomes larger. Running form diagnosis system 200, when calculating the running form score of the test subject, does not need image-capturing system 20 like the one shown in FIG. 1. Therefore, in running form diagnosis system 200, miniaturization of the device necessary for calculating the scores of the test subject is possible. Thus, when the operation expression is registered in advance in information processing device 30A, the test subject can obtain the test score with respect to his own running form, for example, even at home.

[Other Modified Example]

Figure 37:
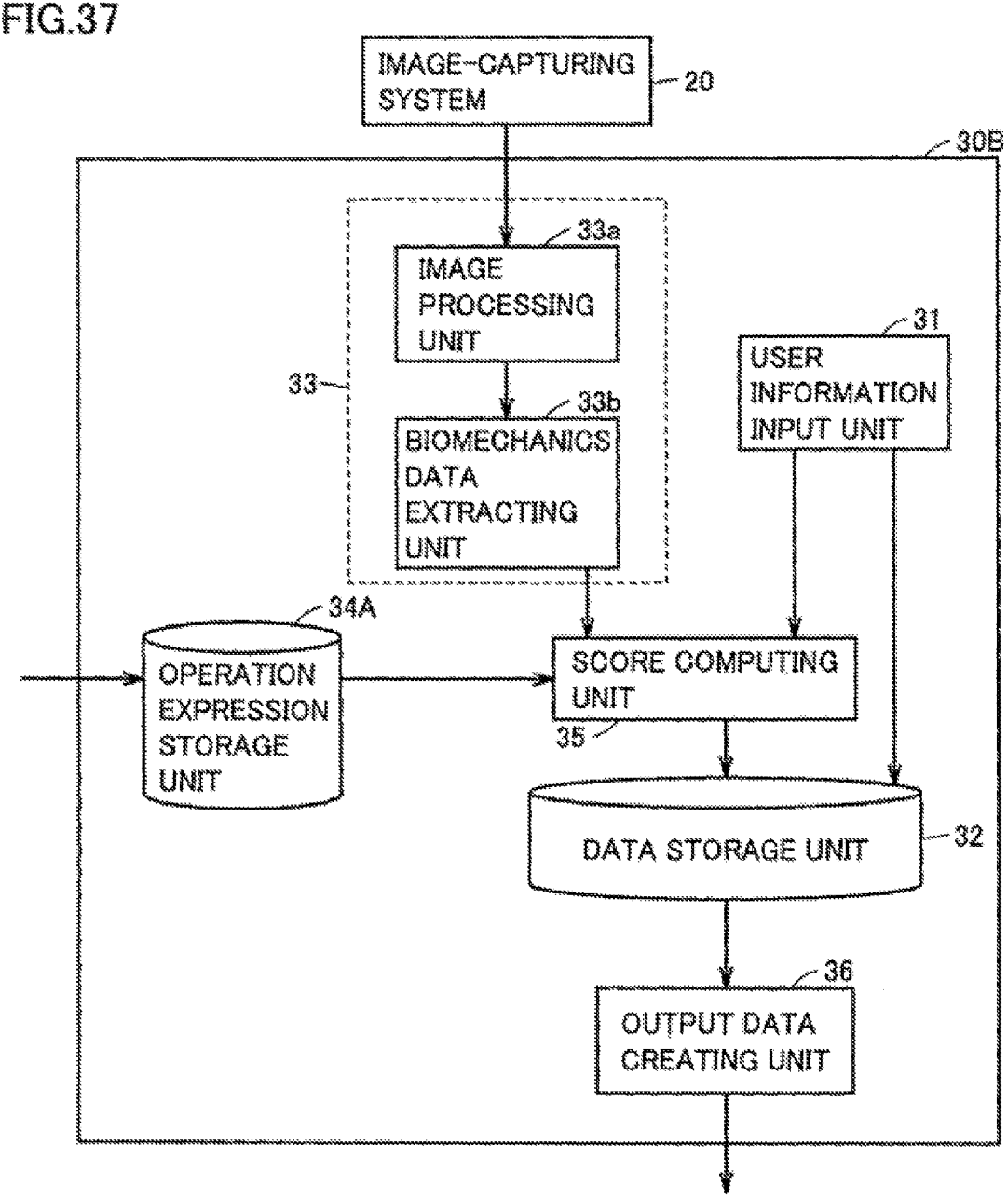
FIG. 37 represents an example of a functional configuration of the information processing device in the case where the operation expression is generated in external equipment.

In the running form diagnosis system, the operation expression is generated by operation expression generating unit 34 of information processing device 30. However, the operation expression may be generated by the process similar to that of operation expression generating unit 34 in external equipment of information processing device 30. FIG. 37 represents functions of information processing device 30B in the case where the operation expression is generated in external equipment. Information processing device 30B is yet another modified example of information processing device 30.

Referring to FIG. 37, in information processing device 30B, information specifying the operation expression is stored in operation expression storage unit 34A. Score computing unit 35, when calculating the running form, reads the operation expression stored in operation expression storage unit 34A.

In the embodiment, example, and modified example, score computing unit 35 may calculate not only the comprehensive score but also the score of the evaluation items of the running form based on the extracted user characteristics (body characteristics and/or biomechanics parameter). More specifically, operation expression storage unit 34A may store information specifying the operation expression for calculating points of each skill element based on the body characteristics or biomechanics parameter. The operation expression as to each skill element is derived by the regression analysis for the case with, for example, the body characteristics and biomechanics data of the test runner as an explanatory variable and the points of each skill element given by the expert with respect to the test runner as an explanatory variable. Score computing unit 35 calculates points as to each skill element by applying parameter Xn (body characteristics and/or biomechanics data) of the test subject extracted in Step S504 of FIG. 18 to the operation expression as to each skill element. The calculated points may be added to the diagnosis result as shown in FIG. 32. In addition to the running form score, points for individual items are presented, so that evaluation of the expert as to the individual items can be also presented. Accordingly, the form diagnosis for the test subject can be performed more in detail.

The running form diagnosis system of the present disclosure generates the operation expressions for evaluating the running form based on correlation between the evaluation of the runner's form by the plurality of experts and the biomechanics data of the runner. Then, the running form diagnosis system scores the running form by applying the characteristics of the test subject to the operation expression. Accordingly, the evaluation of the running form given by the expert, which was considered as implicit knowledge, is embodied in a form of scores through the operation expression. The operation expression is generated based on evaluation of the plurality of experts. Thus, the test subject is provided with scores with respect to the running score automatically. Further, the score which does not deviate enormously from the evaluation given by a plurality of coaches or experts can be provided to the test subject.

The present invention was described in detailed. However, the description is only for illustration and should not be taken as limitation. It will be clearly understood that the scope of the invention is defined by the attached claims.

INDUSTRIAL APPLICABILITY

According to the running form diagnosis system of the present disclosure, it is useful in that the running form of the user can be automatically scored based on a standard equivalent to the determination given by an expert.

REFERENCE SIGNS LIST 10 treadmill; 20 image-capturing system; 30, 30A, 30B information processing device; 31 user information input unit; 32 data storage unit; 33 body information extracting unit; 33a image processing unit; 33b biomechanics data extracting unit; 34 operation expression generating unit; 34A operation expression storage unit; 35 score computing unit; 36 output data creating unit; 40 output device; 50 sensor information input unit; 90 marker; 91 inertial sensor; 100, 200 running form diagnosis system.

The invention claimed is:

1. A running form diagnosis system for scoring a running form of a test subject, comprising:
a storage device configured to store an operation expression representing a correlation between body motion information extracted from information related to running of a plurality of test runners and evaluation given by an expert with respect to respective running of the plurality of test runners;
an interface for receiving an input of information related to running of the test subject; and
a processor configured to output a score as to a running form of said test subject based on information inputted to said interface,
said processor being configured to:
extract body motion information of said test subject from the information related to running of said test subject and inputted to said interface;
calculate the score as to the running form of said test subject by applying said extracted body motion information to said operation expression; and
wherein said operation expression includes:
a first regression expression obtained by performing a regression analysis, with evaluation for two or more items given by said expert with respect to running of said test runners as an explanatory variable and with comprehensive evaluation given by said expert with respect to running of said test runners as an objective variable; and
a second regression expression obtained by performing a regression analysis, with body motion information of said test runners as an explanatory variable and with respective evaluation for said two or more items given by said expert with respect to said test runners as an objective variable.

2. The running form diagnosis system according to claim 1, wherein said two or more items used in said first regression expression are specified from a predetermined number of items by statistically processing evaluation for the predetermined number of items given by said expert with respect to running of said test runners and comprehensive evaluation given by said expert with respect to running of said test runners.

3. The running form diagnosis system according to claim 2, wherein the body motion information of said test runners used in said second regression expression is specified from characteristics of a specified number of items by statistically processing a specified number of body motion information and evaluation of said two or more items.

4. The running form diagnosis system according to claim 1, wherein said operation expression includes a multiple regression expression obtained by performing a multiple regression analysis, with a plurality of body information of said test runners as an explanatory variable and with comprehensive evaluation given by said expert with respect to said test runners as an objective variable.

5. The running form diagnosis system according to claim 1, wherein the body motion information of said test subject includes at least any of an elbow joint angle obtained by calculating an angle of a forearm with respect to an upper arm of said test object, respective segment angles of the forearm and the upper arm of said test subject, a knee joint angle obtained by calculating an angle of a lower leg with respect to an upper leg of said test subject, or respective segment angles of the lower leg and the upper leg of said test subject.

6. The running form diagnosis system according to claim 5, further comprising an image-capturing device coupled to said interface to capture a picture of said test subject,
said interface being configured to receive an input of the picture of said test subject, and
said processor being configured so that:
when extracting at least any of the elbow joint of said test subject or respective segment angles of the forearm and the upper arm of said test subject, said processor extracts these angles based on positions of images of markers attached to a shoulder joint, an elbow joint, and a wrist joint of said test subject in the picture; and
when extracting at least any of the knee joint angle of said test subject or the respective segment angles of the lower leg and the upper leg of said test subject, said processor extracts these angles based on positions of images of markers attached to a base joint, a knee joint, and an ankle joint of said test subject in the picture.

7. The running form diagnosis system according to claim 5, further comprising:
an inertial sensor attached to said test subject;
said interface being configured to receive an input of a detection result of said inertial sensor; and
said processor being configured to extract body motion information of said test subject based on the detection result of said inertial sensor.

8. The running form diagnosis system according to claim 1, wherein said storage device is configured to store advice information as to running in association with scores grouped in advance, and said processor is configured to output said advice information associated with the scores calculated for said test subject.

9. The running form diagnosis system according to claim 1, wherein said operation expression further represents a correlation between body motion information extracted from information related to running of the plurality of test runners as well as body characteristics of said plurality of test runners and comprehensive evaluation given by the expert with respect to respective running of said plurality of test runners, and said interface is configured to receive an input of body characteristics of said test subject, and said processor is configured to calculate a score as to the running form of said test subject by applying the body motion information and body characteristics of said test subject.

10. A method for scoring a running form of a test subject, the method being executed by a computer, said computer including:

a storage device configured to store an operation expression representing correlation between body motion information extracted from information related to running of a plurality of test runners and evaluation given by an expert with respect to respective running of the plurality of test runners; and an interface for receiving an input of information related to running of a test subject, the method comprising:

allowing said computer to extract body motion information of said test subject from information related to running of the test subject and inputted to said interface;

allowing said computer to calculate a score as to the running form of said test subject by applying said extracted body motion information to said operation expression; and wherein said operation expression includes:

a first regression expression obtained by performing a regression analysis, with evaluation for two or more items given by said expert with respect to running of said test runners as an explanatory variable and with a score given by said expert with respect to running of said test runners as an objective variable; and a second regression expression obtained by performing a regression analysis, with body motion information of said test runners as an explanatory variable and with respective evaluation for said two or more items given by said expert with respect to said test runners as an objective variable.

11. The method according to claim 10, wherein said operation expression includes a multiple regression expression obtained by performing a multiple regression analysis, with a plurality of body motion information of said test runners as an explanatory variable and with comprehensive evaluation given by said expert with respect to said test runners as an objective variable.

* * * * *